US012629287B2

(12) United States Patent
Rice et al.

(10) Patent No.: US 12,629,287 B2
(45) Date of Patent: May 19, 2026

(54) TISSUE INTERFACE FOR NEGATIVE PRESSURE AND INSTILLATION THERAPY

(71) Applicant: KCI Manufacturing Unlimited Company, Athlone (IE)

(72) Inventors: Justin Rice, Denver, CO (US); Shannon C. Ingram, Bulverde, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 717 days.

(21) Appl. No.: 17/779,792

(22) PCT Filed: Dec. 3, 2020

(86) PCT No.: PCT/IB2020/061465
§ 371 (c)(1),
(2) Date: May 25, 2022

(87) PCT Pub. No.: WO2021/111369
PCT Pub. Date: Jun. 10, 2021

(65) Prior Publication Data
US 2023/0000688 A1     Jan. 5, 2023

Related U.S. Application Data

(60) Provisional application No. 62/943,588, filed on Dec. 4, 2019.

(51) Int. Cl.
| | |
|---|---|
| *A61F 13/05* | (2024.01) |
| *A61F 13/02* | (2006.01) |
(Continued)

(52) U.S. Cl.
CPC ............ *A61F 13/05* (2024.01); *A61F 13/022* (2013.01); *A61F 13/0289* (2013.01); *A61F 2013/00089* (2013.01)

(58) Field of Classification Search
CPC .............. A61M 1/0092; A61M 1/0088; A61M 1/0049; A61M 39/24; A61F 13/0068;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |
(Continued)

FOREIGN PATENT DOCUMENTS

| | | |
|---|---|---|
| AU | 550575 B2 | 3/1986 |
| AU | 745271 B2 | 3/2002 |
(Continued)

OTHER PUBLICATIONS

Office action for U.S. Appl. No. 16/745,075, dated Jul. 24, 2024.
(Continued)

*Primary Examiner* — Guy K Townsend

(57) ABSTRACT

Dressings, systems, and methods for treating a tissue site are described. The dressing includes a contact layer having a first side and a second side. The first side of the contact layer configured to be positioned adjacent to the tissue site. The contact layer has a plurality of holes extending through the contact layer from the first side to the second side. The dressing includes a cover layer having a first side and a second side. The first side of the cover layer is coupled to the contact layer. The dressing also includes at least one retainer layer removably coupled to the second side of the cover layer.

13 Claims, 12 Drawing Sheets

(51) Int. Cl.
　　*A61F 13/0203* 　　(2024.01)
　　*A61M 39/24* 　　(2006.01)
　　*A61F 13/00* 　　(2006.01)

(58) Field of Classification Search
　　CPC .............. A61F 13/0206; A61F 13/0226; A61F
　　　　　　　　　　　13/0216; A61F 2013/00536; A61F
　　　　　　　　　　　　　　　　　　　　　　　　2013/0094
　　See application file for complete search history.

(56) References Cited

U.S. PATENT DOCUMENTS

| | | | |
|---|---|---|---|
| 2,632,443 A | | 3/1953 | Lesher |
| 2,682,873 A | * | 7/1954 | Everett ............. A61F 13/01029 |
| | | | 604/377 |
| 2,910,763 A | * | 11/1959 | Lauterbach ............ D04H 3/013 |
| | | | 26/18.5 |
| 2,969,057 A | | 1/1961 | Simmons |
| 3,066,672 A | | 12/1962 | Crosby, Jr. et al. |
| 3,367,332 A | | 2/1968 | Groves |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,683,921 A | | 8/1972 | Brooks et al. |
| 3,826,254 A | | 7/1974 | Mellor |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,902,565 A | | 2/1990 | Brook |
| 4,906,233 A | | 3/1990 | Moriuchi et al. |
| 4,906,240 A | | 3/1990 | Reed et al. |
| 4,919,654 A | | 4/1990 | Kalt |

| | | | |
|---|---|---|---|
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,765,123 B2 | | 7/2004 | de Jong et al. |
| 6,814,079 B2 | | 11/2004 | Heaton et al. |
| 7,381,859 B2 | | 6/2008 | Hunt et al. |
| 7,846,141 B2 | | 12/2010 | Weston |
| 7,951,124 B2 | | 5/2011 | Boehringer et al. |
| 8,062,273 B2 | | 11/2011 | Weston |
| 8,216,198 B2 | | 7/2012 | Heagle et al. |
| 8,251,979 B2 | | 8/2012 | Malhi |
| 8,257,327 B2 | | 9/2012 | Blott et al. |
| 8,398,614 B2 | | 3/2013 | Blott et al. |
| 8,449,509 B2 | | 5/2013 | Weston |
| 8,529,548 B2 | | 9/2013 | Blott et al. |
| 8,535,296 B2 | | 9/2013 | Blott et al. |
| 8,551,060 B2 | | 10/2013 | Schuessler et al. |
| 8,568,386 B2 | | 10/2013 | Malhi |
| 8,679,081 B2 | | 3/2014 | Heagle et al. |
| 8,834,451 B2 | | 9/2014 | Blott et al. |
| 8,926,592 B2 | | 1/2015 | Blott et al. |
| 9,017,302 B2 | | 4/2015 | Vitaris et al. |
| 9,168,180 B2 | * | 10/2015 | Ha ..................... A61F 13/00063 |
| 9,198,801 B2 | | 12/2015 | Weston |
| 9,211,365 B2 | | 12/2015 | Weston |
| 9,289,542 B2 | | 3/2016 | Blott et al. |
| 9,421,309 B2 | | 8/2016 | Robinson et al. |
| 9,918,733 B2 | * | 3/2018 | Ingram .................. A61B 17/32 |
| 9,974,694 B2 | | 5/2018 | Locke et al. |
| 10,369,058 B2 | * | 8/2019 | Ha ......................... A61F 13/025 |
| 10,610,414 B2 | * | 4/2020 | Hartwell ................. A61F 13/05 |
| 10,736,788 B2 | | 8/2020 | Locke et al. |
| 10,743,900 B2 | * | 8/2020 | Ingram ................. A61M 1/915 |
| 11,224,542 B2 | | 1/2022 | Robinson et al. |
| 2001/0037118 A1 | | 11/2001 | Shadduck |
| 2002/0065494 A1 | | 5/2002 | Lockwood et al. |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2002/0161346 A1 | * | 10/2002 | Lockwood .............. A61M 1/92 |
| | | | 604/315 |
| 2004/0030304 A1 | | 2/2004 | Hunt et al. |
| 2005/0282895 A1 | | 12/2005 | Dosch et al. |
| 2007/0185426 A1 | | 8/2007 | Ambrosio et al. |

(56)                    References Cited

U.S. PATENT DOCUMENTS

| | | |
|---|---|---|
| 2008/0132819 A1 | 6/2008 | Radl et al. |
| 2008/0177253 A1 | 7/2008 | Boehringer et al. |
| 2008/0275409 A1 | 11/2008 | Kane et al. |
| 2008/0300555 A1 | 12/2008 | Olson et al. |
| 2009/0012482 A1 | 1/2009 | Pinto et al. |
| 2009/0069760 A1 | 3/2009 | Finklestein |
| 2009/0093779 A1 | 4/2009 | Riesinger |
| 2009/0227969 A1* | 9/2009 | Jaeb ........................ A61F 13/05 |
| | | 604/313 |
| 2009/0299303 A1 | 12/2009 | Seegert |
| 2010/0063484 A1 | 3/2010 | Heagle |
| 2010/0160871 A1 | 6/2010 | Seegert et al. |
| 2010/0160874 A1 | 6/2010 | Robinson et al. |
| 2010/0160876 A1 | 6/2010 | Robinson et al. |
| 2010/0185163 A1 | 7/2010 | Heagle |
| 2010/0312159 A1 | 12/2010 | Aali et al. |
| 2011/0015619 A1* | 1/2011 | Svedman ............. A61M 1/882 |
| | | 514/772.3 |
| 2011/0054422 A1* | 3/2011 | Locke .................. A61M 1/915 |
| | | 604/319 |
| 2011/0087176 A2 | 4/2011 | Blott et al. |
| 2011/0118683 A1 | 5/2011 | Weston |
| 2011/0178451 A1 | 7/2011 | Robinson et al. |
| 2011/0213287 A1 | 9/2011 | Lattimore et al. |
| 2011/0213319 A1 | 9/2011 | Blott et al. |
| 2011/0230809 A1* | 9/2011 | Manwaring ............. A61P 17/02 |
| | | 604/319 |
| 2011/0282309 A1 | 11/2011 | Adie et al. |
| 2011/0301556 A1 | 12/2011 | Lichtenstein |
| 2012/0016334 A1 | 1/2012 | Nakajima et al. |
| 2012/0143113 A1 | 6/2012 | Robinson et al. |
| 2012/0143114 A1 | 6/2012 | Locke et al. |
| 2012/0157945 A1 | 6/2012 | Robinson et al. |
| 2013/0144230 A1 | 6/2013 | Wu et al. |
| 2013/0211349 A1 | 8/2013 | Stokes et al. |
| 2013/0274717 A1 | 10/2013 | Dunn |
| 2014/0066868 A1 | 3/2014 | Freedman et al. |
| 2014/0155791 A1 | 6/2014 | Robinson et al. |
| 2014/0163491 A1 | 6/2014 | Schuessler et al. |
| 2014/0228787 A1 | 8/2014 | Croizat et al. |
| 2014/0236112 A1 | 8/2014 | Von Wolff et al. |
| 2015/0080788 A1 | 3/2015 | Blott et al. |
| 2015/0119832 A1* | 4/2015 | Locke ............... A61F 13/00063 |
| | | 604/319 |
| 2015/0174284 A1 | 6/2015 | Payne et al. |
| 2015/0201954 A1 | 7/2015 | Pratt et al. |
| 2015/0320434 A1* | 11/2015 | Ingram ................... A61M 1/85 |
| | | 606/131 |
| 2015/0320602 A1 | 11/2015 | Locke et al. |
| 2015/0320603 A1 | 11/2015 | Locke et al. |
| 2016/0022885 A1 | 1/2016 | Dunn et al. |
| 2016/0038345 A1* | 2/2016 | Ha ....................... A61F 13/0226 |
| | | 602/54 |
| 2016/0095754 A1 | 4/2016 | Andrews et al. |
| 2016/0158066 A1 | 6/2016 | Chao |
| 2016/0175156 A1 | 6/2016 | Locke et al. |
| 2016/0354086 A1 | 12/2016 | Dunn |
| 2017/0007462 A1 | 1/2017 | Hartwell et al. |
| 2017/0135862 A1 | 5/2017 | Tuck et al. |
| 2017/0189237 A1 | 7/2017 | Locke et al. |
| 2017/0197006 A1 | 7/2017 | Johnson et al. |
| 2017/0231822 A1 | 8/2017 | Hoggarth et al. |
| 2017/0239095 A1 | 8/2017 | Hoggarth et al. |
| 2018/0235646 A1 | 8/2018 | Locke et al. |
| 2018/0353337 A1* | 12/2018 | Locke ................. A61F 13/0213 |
| 2018/0353338 A1 | 12/2018 | Locke et al. |
| 2018/0353662 A1* | 12/2018 | Locke ................. A61F 13/0206 |
| 2019/0117465 A1* | 4/2019 | Osborne ................. A61F 13/05 |
| 2019/0192350 A1 | 6/2019 | Gowans et al. |
| 2019/0231944 A1 | 8/2019 | Dunn et al. |
| 2019/0274889 A1* | 9/2019 | Steward .............. A61F 13/0286 |
| 2019/0314209 A1* | 10/2019 | Ha ....................... A61F 13/0233 |
| 2020/0046567 A1* | 2/2020 | Carroll .................... A61M 1/90 |
| 2020/0107965 A1 | 4/2020 | Greener |

| | | |
|---|---|---|
| 2020/0146896 A1* | 5/2020 | Rice ...................... A61M 1/915 |
| 2020/0155359 A1* | 5/2020 | Carroll .............. A61F 13/00051 |
| 2020/0383837 A1 | 12/2020 | Gowans et al. |
| 2021/0077302 A1* | 3/2021 | Carroll .................. A61M 1/915 |
| 2021/0228417 A1* | 7/2021 | Ha ..................... A61F 13/00059 |
| 2023/0000687 A1* | 1/2023 | Rice ................... A61F 13/0233 |
| 2023/0000688 A1* | 1/2023 | Rice ...................... A61F 13/022 |
| 2024/0099898 A1* | 3/2024 | Rice ........................ A61F 13/02 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| EP | 3263079 A1 | 1/2018 |
| EP | 3378450 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 01/85248 A1 | 11/2001 |
| WO | 2005102234 A2 | 11/2005 |
| WO | 2006114638 A2 | 11/2006 |
| WO | 2008/005532 A2 | 1/2008 |
| WO | 2008136998 A1 | 11/2008 |
| WO | 2009021523 A1 | 2/2009 |
| WO | 2009/146441 A1 | 12/2009 |
| WO | 2010051071 A1 | 5/2010 |
| WO | 2010051073 A1 | 5/2010 |
| WO | 2010075178 A2 | 7/2010 |
| WO | 2011008497 A2 | 1/2011 |
| WO | 2011089098 A1 | 7/2011 |
| WO | 2013/032745 A1 | 3/2013 |
| WO | 2013066426 A2 | 5/2013 |
| WO | 2013071243 A2 | 5/2013 |
| WO | 2013116552 A1 | 8/2013 |
| WO | 2013129343 A1 | 9/2013 |
| WO | 2013149078 A1 | 10/2013 |
| WO | 2014/014922 A1 | 1/2014 |
| WO | 2014014871 A1 | 1/2014 |
| WO | 2014024048 A1 | 2/2014 |
| WO | 2014143487 A1 | 9/2014 |
| WO | 2015172104 A1 | 11/2015 |
| WO | 2015172111 A1 | 11/2015 |
| WO | 2015173547 A1 | 11/2015 |
| WO | 2017195038 A1 | 11/2017 |
| WO | 2018/077872 A1 | 5/2018 |
| WO | 2018/094061 A1 | 5/2018 |
| WO | 2018/226328 A1 | 12/2018 |
| WO | 2019136164 A1 | 7/2019 |

US 12,629,287 B2

Page 4

(56) References Cited

FOREIGN PATENT DOCUMENTS

WO      2019152422  A1    8/2019
WO      2020097529  A1    5/2020

OTHER PUBLICATIONS

Japanese Decision of Rejection and Decision for Dismissal of Amendment for Application No. 2021-524440, dated Oct. 15, 2024.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, The Use of Hypermia in the Postoperative Treatment of Lesions of the Extremities and Thorax, Journal of the American Medical Association 64 (1915), pp. 1548-1549.
Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
Office action for U.S. Appl. No. 16/678,450, dated Sep. 9, 2024.
Office Action for related U.S. Appl. No. 16/678,450, dated Jul. 31, 2023.
Office Action for related U.S. Appl. No. 16/923,651, dated Aug. 28, 2023.
Office action for related U.S. Appl. No. 16/918,682, dated Sep. 21, 2023.
Japanese Notice of Rejection for Application No. 2021-542412, dated Dec. 5, 2023.

(56) References Cited

OTHER PUBLICATIONS

European Examination Report for Application No. 20747133.5, dated Dec. 21, 2023.
Office action for related U.S. Appl. No. 16/923,651 dated Feb. 12, 2024.
Japanese Notice of Rejection for Application No. 2019-233695 dated Mar. 5, 2024.
Office action for related U.S. Appl. No. 17/629,174, dated Mar. 26, 2024.
Japanese Notice of Rejection for Application No. 2021-524440 dated Apr. 16, 2024.
International Search Report and Written Opinion Corresponding to Application No. PCT/IB2020/061465, mailed Mar. 16, 2021.
Partial International Search Report from PCT/US2015/030030 mailed Jul. 22, 2015.
International Search Report and Written Opinion for PCT/US2015/030023 mailed Aug. 24, 2015.
Extended European Search Report for corresponding Application No. 171862527, mailed Nov. 14, 2017.
"Introduction to Polyurethanes: Thermoplastic Polyurethane", American Chemistry Council, 2018, https://polyurethane.americanchemistry.com/polyurethanes/Introduction-to-Polyurethanes/Applications/Thermoplastic-Polyurethane/.
International Search Report and Written Opinion for PCT/US2015/030027 mailed Jul. 15, 2015.
International Search Report and Written Opinion for corresponding Application No. PCT/US2019/027463, mailed Jul. 4, 2019.
Japanese Notice of Rejection for corresponding Application No. 2016-566815, mailed Feb. 5, 2019.
Extended European Search Report for corresponding Application No. 18162504.7, mailed May 24, 2018.
Japanese Notice of Rejection for corresponding Application No. 2016-566785, mailed Jun. 25, 2019.
Japanese Notice of Rejection for corresponding Application No. 2016-566785, mailed Jan. 29, 2019.

Non-Final Office Action for Corresponding U.S. Appl. No. 15/960,310, mailed Apr. 29, 2020.
Japanese Notice of Rejection for Corresponding Application No. 2019-233695, mailed Oct. 13, 2020.
International Search Report and Written Opinion for Corresponding Application No. PCT/US2019/060567, mailed Feb. 14, 2020.
International Search Report and Written Opinion for Corresponding Application No. PCT/US2019/045505, mailed Nov. 7, 2019.
International Search Report and Written Opinion for Corresponding Application No. PCT/US2019/060479, mailed Apr. 7, 2020.
International Search Report and Written Opinion for Corresponding Application No. PCT/US2020/013922, mailed May 4, 2020.
Chinese Notice of Rejection Corresponding to Application No. 2020800099951, mailed Mar. 28, 2022.
International Search Report and Written Opinion for Corresponding Application No. PCT/IB2020/056911, mailed Oct. 21, 2020.
International Search Report and Written Opinion Corresponding to Application No. PCT/IB2020/061435, mailed Mar. 16, 2021.
International Search Report and Written Opinion Corresponding to Application No. PCT/IB2020/061540, mailed Feb. 24, 2021.
Canadian Examination Report for related application 2,947,302, dated Jun. 11, 2021.
Japanese Notice of Rejection for related application 2020-557257, dated Feb. 28, 2023.
Office action for U.S. Appl. No. 16/918,682, dated Jan. 2, 2025.
Copper Development Association Inc., Introduction to Antimicrobial Copper, Feb. 15, 2024.
Office action for U.S. Appl. No. 17/629,174, dated Feb. 26, 2025.
Office action for U.S. Appl. No. 17/779,755, dated Apr. 9, 2025.
Office Action for related U.S. Appl. No. 18/538,282, dated Nov. 10, 2025.
Office Action for related U.S. Appl. No. 17/779,755, dated Jan. 8, 2026.
Office Action for related U.S. Appl. No. 16/745,075, dated Jan. 28, 2026.

* cited by examiner

TISSUE INTERFACE FOR NEGATIVE PRESSURE AND INSTILLATION THERAPY

CROSS-REFERENCE TO RELATED APPLICATIONS

This application claims the benefit of priority to U.S. Provisional Application No. 62/943,588, filed on Dec. 4, 2019, which is incorporated herein by reference in its entirety.

TECHNICAL FIELD

The invention set forth in the appended claims relates generally to tissue treatment systems and more particularly, but without limitation, to a dressing for the removal of thick exudate in a negative-pressure therapy environment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for disposition of a negative-pressure dressing in a negative-pressure therapy environment are set forth in the appended claims. Illustrative embodiments are also provided to enable a person skilled in the art to make and use the claimed subject matter.

For example, in some embodiments, a dressing for treating a tissue site is described. The dressing can include a contact layer having a first side and a second side. The first side of the contact layer can be configured to be positioned adjacent to the tissue site. The contact layer can have a plurality of holes extending through the contact layer from the first side to the second side. The dressing can include a cover layer having a first side and a second side. The first side of the cover layer can be coupled to the contact layer. The dressing can also include at least one retainer layer removably coupled to the second side of the cover layer.

A method of manufacturing a dressing for a tissue site is also described herein. A first layer of foam can be provided and a sheet of adhesive can be coupled to a side of the first layer of foam. A plurality of holes can be formed in the first layer of foam and the sheet of adhesive, and a second layer of foam can be positioned adjacent to the sheet of adhesive. The sheet of adhesive can be activated. A third layer of foam can be provided, and the third layer of foam can be removably coupled to a side of the second layer of foam opposite of the first layer of foam.

Alternatively, other example embodiments may describe a system for treating a tissue site. The system can include a tissue interface, a sealing member configured to be positioned over the tissue interface and sealed to tissue surrounding the tissue site, and a therapy source configured to be fluidly coupled to the tissue interface through the sealing member. The tissue interface can include a debridement tool having a first side and a second side, the first side configured to be positioned adjacent to the tissue site. The debridement tool can have a plurality of perforations extending through the debridement tool from the first side to the second side. The tissue interface can also include a cover layer having a first side and a second side, the first side coupled to the second side of the debridement tool. At least one retainer layer can be removably coupled to the second side of the cover layer.

Another dressing for treating a tissue site may be described. The dressing can include a contact layer having a first side and a second side, the first side configured to be positioned adjacent to the tissue site. The contact layer can have a plurality of holes extending through the contact layer from the first side to the second side. The dressing can include a cover layer having a first side and a second side. The first side can be coupled to the contact layer. A protective layer having a first side and a second side can be removably coupled to the cover layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such as injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

Figure 1:
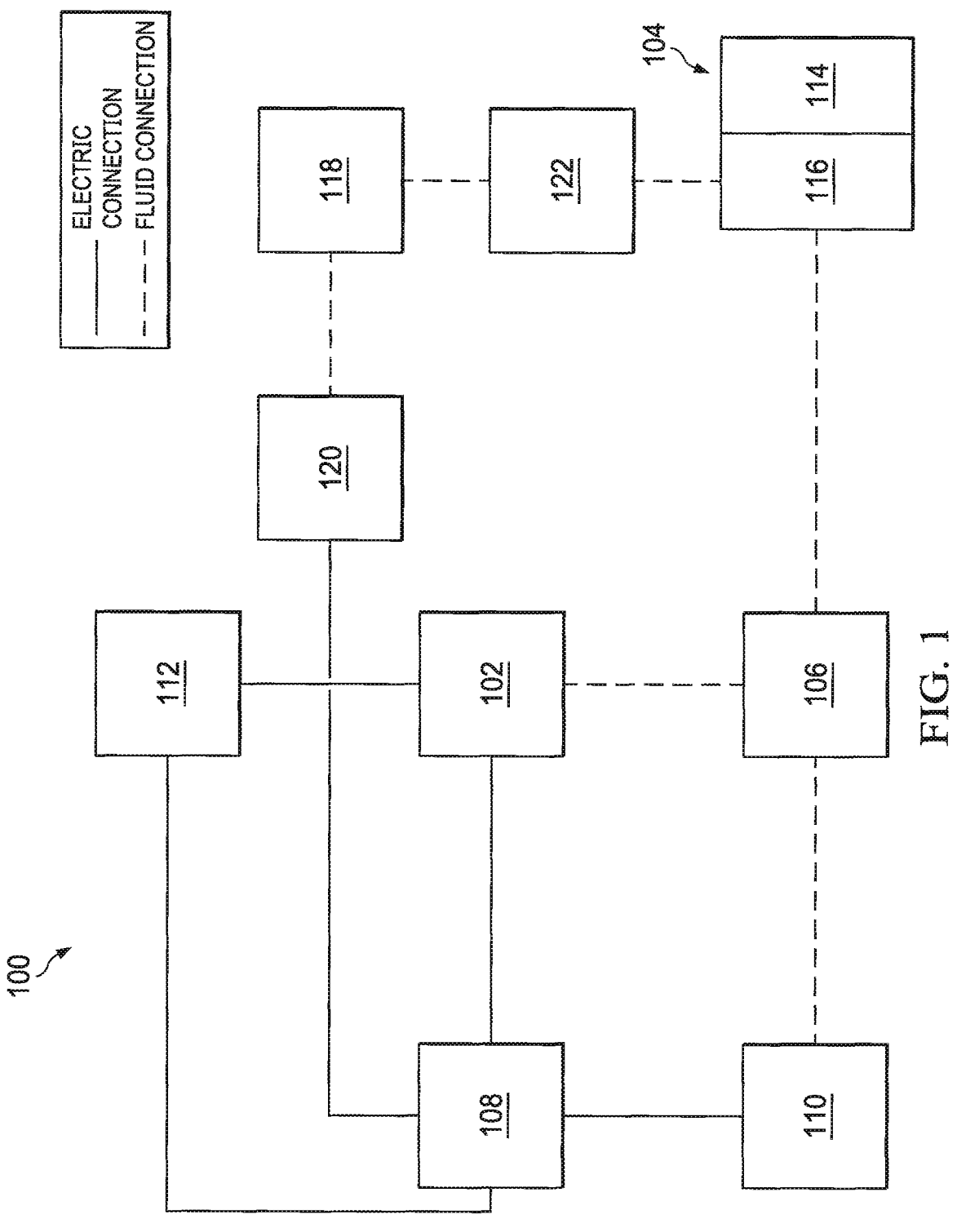
FIG. 1 is a simplified functional block diagram of an example embodiment of a therapy system that can provide negative-pressure therapy with instillation of topical treatment solutions to a tissue site in accordance with this specification.

FIG. 1 is a simplified functional block diagram of an example embodiment of a therapy system 100 that can provide negative-pressure therapy with instillation of topical treatment solutions to a tissue site in accordance with this specification. The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. As illustrated in the example of FIG. 1, the dressing 104 may comprise or consist essentially of a tissue interface 114, a cover 116, or both in some embodiments.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as a positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline or sterile water) to a tissue site. For example, the instillation regulator 122 may comprise a piston that can be pneumatically actuated by the negative-pressure source 102 to draw instillation solution from the solution source 118 during a negative-pressure interval and to instill the solution to the dressing 104 during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108, and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108, and may be fluidly coupled to one or more distribution components to provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least about 300 g/m² per twenty-four hours in some embodiments. In some example embodiments, the cover 116 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

The cover 116 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Coveris Advanced Coatings of Wrexham, United Kingdom having, for example, an MVTR (inverted cup technique) of about 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Glendale, California;

polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between about 25 grams per square meter (g.s.m.) and about 65 g.s.m. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organ gel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

During treatment of a tissue site, some tissue sites may not heal according to the normal medical protocol and may develop areas of necrotic tissue. Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. Necrotic tissue may also include eschar. Eschar may be a portion of necrotic tissue that has become dehydrated and hardened. Eschar may be the result of a burn injury, gangrene, ulcers, fungal infections, spider bites, or anthrax. Eschar may be difficult to remove without the use of surgical cutting instruments.

In addition to necrotic tissue, slough, and eschar, the tissue site may include biofilms, lacerated tissue, devitalized tissue, contaminated tissue, damaged tissue, infected tissue, exudate, highly viscous exudate, fibrinous slough and/or other material that can generally be referred to as debris. The debris may inhibit the efficacy of tissue treatment and slow the healing of the tissue site. If the debris is in the tissue site, the tissue site may be treated with different processes to disrupt the debris. Examples of disruption can include softening of the debris, separation of the debris from desired tissue, such as the subcutaneous tissue, preparation of the debris for removal from the tissue site, and removal of the debris from the tissue site.

The debris can require debridement performed in an operating room. In some cases, tissue sites requiring debridement may not be life-threatening, and debridement may be considered low-priority. Low-priority cases can experience delays prior to treatment as other, more life-threatening, cases may be given priority for an operating room. As a result, low priority cases may need temporization. Temporization can include stasis of a tissue site that limits deterioration of the tissue site prior to other treatments, such as debridement, negative-pressure therapy or instillation.

When debriding, clinicians may find it difficult to define separation between healthy, vital tissue and necrotic tissue. As a result, normal debridement techniques may remove too much healthy tissue or not enough necrotic tissue. If non-viable tissue demarcation does not extend deeper than the deep dermal layer, or if the tissue site is covered by the debris, such as slough or fibrin, gentle methods to remove the debris should be considered to avoid excess damage to the tissue site.

In some debridement processes, a mechanical process is used to remove the debris. Mechanical processes may include using scalpels or other cutting tools having a sharp edge to cut away the debris from the tissue site. Other mechanical processes may use devices that can provide a stream of particles to impact the debris to remove the debris in an abrasion process, or jets of high pressure fluid to impact the debris to remove the debris using water jet cutting or lavage. Typically, mechanical processes of debriding a tissue site may be painful and may require the application of local anesthetics. Mechanical processes also risk over removal of healthy tissue that can cause further damage to the tissue site and delay the healing process.

Debridement may also be performed with an autolytic process. For example, an autolytic process may involve using enzymes and moisture produced by a tissue site to soften and liquefy the necrotic tissue and debris. Typically, a dressing may be placed over a tissue site having debris so that fluid produced by the tissue site may remain in place, hydrating the debris. Autolytic processes can be pain-free, but autolytic processes are a slow and can take many days. Because autolytic processes are slow, autolytic processes may also involve many dressing changes. Some autolytic processes may be paired with negative-pressure therapy so that, as debris hydrates, negative pressure supplied to a tissue site may draw off the debris. In some cases, a manifold positioned at a tissue site to distribute negative-pressure across the tissue site may become blocked or clogged with debris broken down by an autolytic process. If a manifold becomes clogged, negative-pressure may not be able to remove debris, which can slow or stop the autolytic process.

Debridement may also be performed by adding enzymes or other agents to the tissue site that digest tissue. Often, strict control of the placement of the enzymes and the length of time the enzymes are in contact with a tissue site must be maintained. If enzymes are left on a tissue site for longer than needed, the enzymes may remove too much healthy tissue, contaminate the tissue site, or be carried to other areas of a patient. Once carried to other areas of a patient, the enzymes may break down undamaged tissue and cause other complications.

Furthermore, some dressings for treating a tissue site may include multiple layers and require sizing of the dressing during placement of the dressing at the tissue site. For example, several layers may be needed to completely fill a tissue site prior to placement of a cover to seal the tissue site. Each layer may be individually sized and then placed into the tissue site. Sizing each individual layer may increase the risk of contamination of the layer by foreign bodies in the environment and contamination of the tissue site from errant material from the dressing produced during the sizing process. If there is a preferred order for the layers of the dressing, placing each layer of the dressing individually may lead to improper dressing application. For example, a particular layer may have a special coating requiring a particular placement within a stack of layers that form the dressing. Placing each layer of the dressing individually provides an opportunity for a user to become confused and place the layer in a sub-optimal position within the dressing. This may lead to treatment that has a decreased effectiveness.

These limitations and others may be addressed by the therapy system 100, which can provide negative-pressure therapy, instillation therapy, and disruption of debris. In some embodiments, the therapy system 100 can provide mechanical movement at a surface of the tissue site in combination with cyclic delivery and dwell of topical solutions to help solubilize debris. For example, a negative-pressure source may be fluidly coupled to a tissue site to provide negative pressure to the tissue site for negative-pressure therapy. In some embodiments, a fluid source may be fluidly coupled to a tissue site to provide therapeutic fluid to the tissue site for instillation therapy. In some embodiments, the therapy system 100 may include a contact layer positioned adjacent to a tissue site that may be used with negative-pressure therapy, instillation therapy, or both to disrupt areas of a tissue site having debris. Following the disruption of the debris, negative-pressure therapy, instillation therapy, and other processes may be used to remove the debris from a tissue site. In some embodiments, the therapy system 100 may be used in conjunction with other tissue removal and debridement techniques. For example, the therapy system 100 may be used prior to enzymatic debridement to soften the debris. In another example, mechanical debridement may be used to remove a portion of the debris at the tissue site, and the therapy system 100 may then be used to remove the remaining debris while reducing the risk of trauma to the tissue site. The therapy system 100 may also provide a dressing that may be applied in fewer steps so as to limit opportunities for contamination of the tissue site and the dressing, and decrease instances of improper placement, thereby increasing the effectiveness of the therapy system 100.

Figure 2:
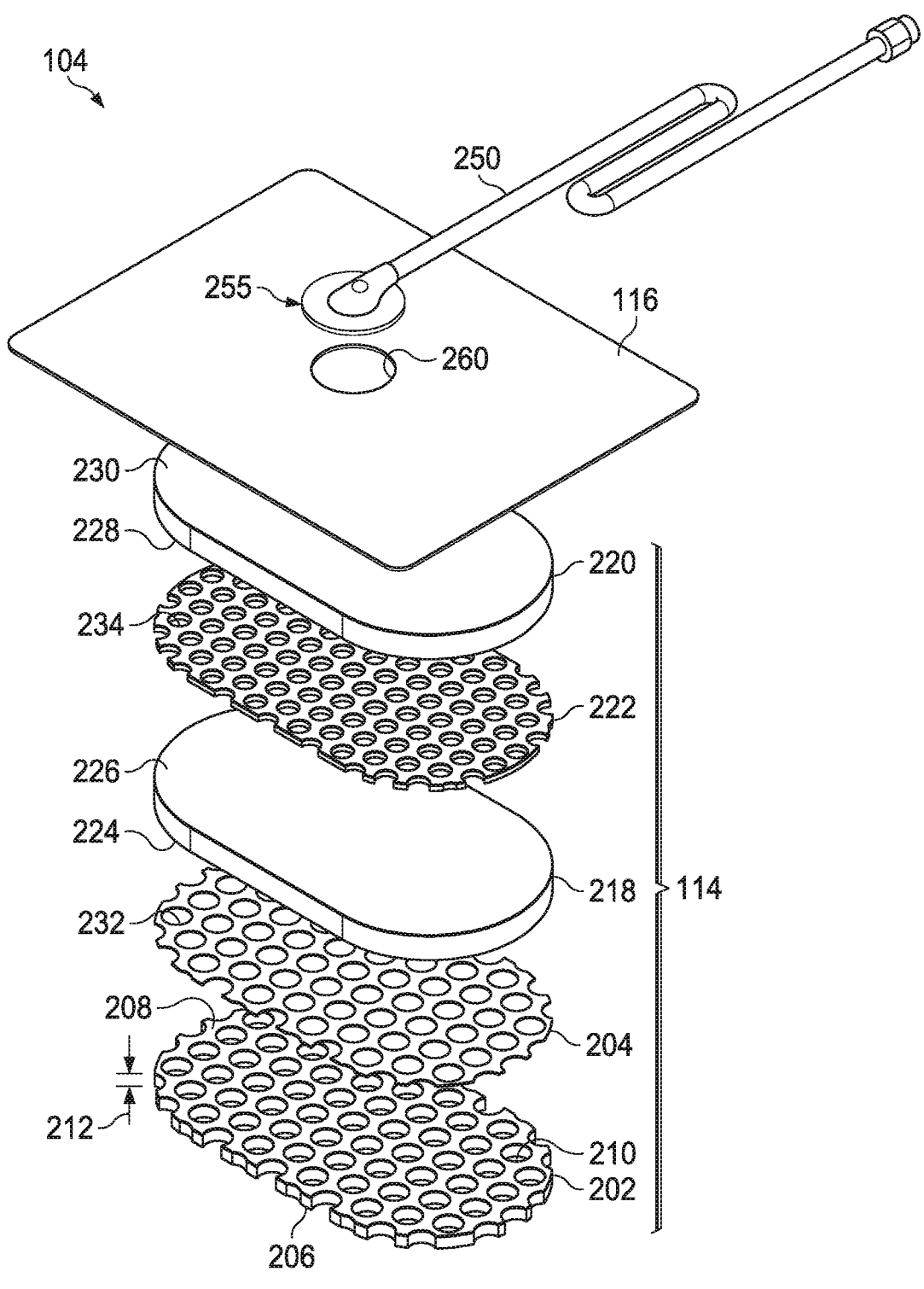
FIG. 2 is an assembly view of an example of a dressing of FIG. 1, illustrating additional details that may be associated with some embodiments in which a tissue interface comprises multiple layers.

FIG. 2 is an assembly view of an example of the dressing 104 of FIG. 1, illustrating additional details that may be associated with some embodiments in which the tissue interface 114 comprises multiple layers. In some embodiments, the tissue interface 114 can include a contact layer 202, an adhesive layer 204, a first retainer layer 218, a coupling layer 222, and a second retainer layer 220. The contact layer 202 may have a first surface 206, a second surface 208, and a plurality of through-holes 210 extending through the contact layer 202 from the first surface 206 to the second surface 208. The adhesive layer 204 may be disposed adjacent to the second surface 208 of the contact layer 202. In some embodiments, the adhesive layer 204 can be coupled to the second surface 208 of the contact layer 202.

The first retainer layer 218 may have a first surface 224 and a second surface 226. The second retainer layer 220 may have a first surface 228 and a second surface 230. An adhering layer, such as the coupling layer 222, may couple the first retainer layer 218 to the second retainer layer 220. The second surface 226 of the first retainer layer 218 may be coupled to the coupling layer 222, and the first surface 228 of the second retainer layer 220 may be coupled to the coupling layer 222. The adhesive layer 204 may be disposed adjacent to the first surface 224 of the first retainer layer 218. In some embodiments, the adhesive layer 204 can be coupled to the first surface 224 of the first retainer layer 218. In some embodiments, the first retainer layer 218 may be positioned over the contact layer 202.

A debridement tool, such as the contact layer 202 may have a substantially uniform thickness 212. In some embodiments, the thickness 212 may be between about 7 mm and about 15 mm. In other embodiments, the thickness 212 may be thinner or thicker than the stated range as needed for the particular application of the dressing 104. In a preferred embodiment, the thickness 212 may be about 8 mm. In some embodiments, individual portions of the contact layer 202 may have a minimal tolerance from the thickness 212. In some embodiments, the thickness 212 may have a tolerance of about 2 mm. In some embodiments, the thickness 212 may be between about 6 mm and about 10 mm. The contact layer 202 may be flexible so that the contact layer 202 can be contoured to a surface of the tissue site.

In some embodiments, the contact layer 202 may be formed from thermoplastic elastomers (TPE), such as styrene ethylene butylene styrene (SEBS) copolymers, or thermoplastic polyurethane (TPU). The contact layer 202 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the contact layer 202. In some embodiments, sheets of TPE or TPU having a thickness between about 0.2 mm and about 2.0 mm may be used to form a structure having the thickness 212. In some embodiments, the contact layer 202 may be formed from a 3D textile, also referred to as a spacer fabric. Suitable 3D textiles may be produced by Heathcoat Fabrics, Ltd., Baltex, and Mueller Textil Group. The contact layer 202 can also be formed from polyurethane, silicone, polyvinyl alcohol, and metals, such as copper, tin, silver or other beneficial metals.

In some embodiments, the contact layer 202 may be formed from a foam. For example, cellular foam, open-cell foam, reticulated foam, or porous tissue collections, may be used to form the contact layer 202. In some embodiments, the contact layer 202 may be formed of V.A.C.® GRANUFOAM™ Dressing, grey foam, or a type of Zotefoams. Grey foam may be a polyester polyurethane foam having about 60 pores per inch (ppi). Zotefoams may be a closed-cell crosslinked polyolefin foam. In one non-limiting example, the contact layer 202 may be an open-cell, reticulated polyurethane foam such as V.A.C.® GRANUFOAM™ Dressing available from Kinetic Concepts, Inc. of San Antonio, Texas; in other embodiments, the contact layer 202 may be an open-cell, reticulated polyurethane foam such as a V.A.C. VERAFLO™ dressing, also available from Kinetic Concepts, Inc., of San Antonio, Texas. In some embodiments, the contact layer 202 may have a 25% compression load deflection of at least 0.35 pounds per square inch, and the 65% compression load deflection may be at least 0.43 pounds per square inch. In some embodiments, the tensile strength of the contact layer 202 may be at least 10 pounds per square inch. The contact layer 202 may have a tear strength of at least 2.5 pounds per inch.

In some embodiments, the contact layer 202 may be formed from a foam that is mechanically or chemically compressed, often as part of a thermoforming process, to increase the density of the foam at ambient pressure. A foam that is mechanically or chemically compressed may be referred to as a compressed foam or a felted foam. A compressed foam may be characterized by a firmness factor (FF) that is defined as a ratio of the density of a foam in a compressed state to the density of the same foam in an uncompressed state. For example, a firmness factor (FF) of 5 may refer to a compressed foam having a density at ambient pressure that is five times greater than a density of the same foam in an uncompressed state at ambient pressure. Generally a compressed or felted foam may have a firmness factor greater than 1.

Mechanically or chemically compressing a foam may reduce a thickness of the foam at ambient pressure when compared to the same foam that has not been compressed. Reducing a thickness of a foam by mechanical or chemical compression may increase a density of the foam, which may increase the firmness factor (FF) of the foam. Increasing the firmness factor (FF) of a foam may increase a stiffness of the foam in a direction that is parallel to a thickness of the foam. For example, increasing a firmness factor (FF) of the contact layer 202 may increase a stiffness of the contact layer 202 in a direction that is parallel to the thickness 212 of the contact layer 202. In some embodiments, a compressed foam may be a compressed V.A.C.® GRANUFOAM™ Dressing. V.A.C.® GRANUFOAM™ Dressing may have a density of about 0.03 grams per centimeter³ (g/cm³) in its uncompressed state. If the V.A.C.® GRANUFOAM™ Dressing is compressed to have a firmness factor (FF) of 5, the V.A.C.® GRANUFOAM™ Dressing may be compressed until the density of the V.A.C.® GRANUFOAM™ Dressing is about 0.15 g/cm³. V.A.C.® VERAFLO™ dressing may also be compressed to form a compressed foam having a firmness factor (FF) up to 5. In some embodiments, the contact layer 202 may have a thickness between about 4 mm and about 15 mm, and more specifically, about 8 mm at ambient pressure. In an exemplary embodiment, if the thickness 212 of the contact layer is about 8 mm, and the contact layer 202 is positioned within the sealed environment and subjected to negative pressure of about −115 mm Hg to about −135 mm Hg, the thickness 212 of the contact layer 202 may be between about 1 mm and about 5 mm and, generally, greater than about 3 mm.

The firmness factor (FF) may also be used to compare compressed foam materials with non-foam materials. For example, a Supracor® material may have a firmness factor (FF) that allows Supracor® to be compared to compressed foams. In some embodiments, the firmness factor (FF) for a non-foam material may represent that the non-foam material has a stiffness that is equivalent to a stiffness of a compressed foam having the same firmness factor. For example, if a contact layer is formed from Supracor®, as illustrated in Table 1 below, the contact layer may have a stiffness that is about the same as the stiffness of a compressed V.A.C.® GRANUFOAM™ Dressing material having a firmness factor (FF) of 3.

Generally, if a compressed foam is subjected to negative pressure, the compressed foam exhibits less deformation than a similar uncompressed foam. If the contact layer 202 is formed of a compressed foam, the thickness 212 of the contact layer 202 may deform less than if the contact layer 202 is formed of a comparable uncompressed foam. The decrease in deformation may be caused by the increased stiffness as reflected by the firmness factor (FF). If subjected to the stress of negative pressure, the contact layer 202 that is formed of compressed foam may flatten less than the contact layer 202 that is formed from uncompressed foam. Consequently, if negative pressure is applied to the contact layer 202, the stiffness of the contact layer 202 in the direction parallel to the thickness 212 of the contact layer 202 allows the contact layer 202 to be more compliant or compressible in other directions, e.g., a direction perpendicular to the thickness 212. The foam material used to form a compressed foam may be either hydrophobic or hydrophilic. The foam material used to form a compressed foam may also be either reticulated or un-reticulated. The pore size of a foam material may vary according to needs of the contact layer 202 and the amount of compression of the foam. For example, in some embodiments, an uncompressed foam may have pore sizes in a range of about 400 microns to about 600 microns. If the same foam is compressed, the pore sizes may be smaller than when the foam is in its uncompressed state.

A joining layer, such as the adhesive layer 204 may be a layer of adhesive disposed on the contact layer 202. In some embodiments, the adhesive layer 204 may be coincident with the contact layer 202. The adhesive layer 204 may include a plurality of through-holes 232. The through-holes 232 may have a same size and shape as the through-holes 210. Preferably, the through-holes 232 are aligned with the through-holes 210 so that edges of the through-holes 232 and the through-holes 210 are coincident. In some embodiments, the adhesive layer 204 may be free of the through-holes 232 and can cover the through-holes 210 of the contact layer 202. In other embodiments, the through-holes 210 of the contact layer 202 and the through-holes 232 of the adhesive layer 204 can be formed after the adhesive layer 204 is coupled to the contact layer 202.

The adhesive of the adhesive layer 204 may have a bond strength greater than or equal to about the tensile strength of the materials coupled to the adhesive layer 204. For example, the adhesive layer 204 may have a bond strength greater than or equal to the tensile strength of the contact layer 202 and the first retainer layer 218. In some embodiments, the tensile strength of one or both of the contact layer 202 and the first retainer layer 218 may be at least 10 pounds per square inch. In some embodiments, the adhesive layer 204 may have a thickness between about 215 microns and about 240 microns. The adhesive layer 204 may be a hot melt adhesive. For example, the adhesive layer 204 can be an Advantage Hot Melt Adhesive produced by HMT Manufacturing, Inc. Other adhesives may be used provided that, following the coupling of the contact layer 202 to the first retainer layer 218 by the adhesive layer 204 to form the tissue interface 114, an occlusion rate of the contact layer 202 and the first retainer layer 218 is less than about 50%. An occlusion rate may refer to the proportion of a foam material having pores which are blocked or occluded. An occlusion rate of less than 50% will have less than one-half of the pores of the foam material that are occluded.

In some embodiments, the first retainer layer 218 may be a cover layer, and the second retainer layer 220 may be a protective layer. Both the first retainer layer 218 and the second retainer layer 220 may be a foam having pore sizes in a range of about 60 microns to about 2000 microns. In other embodiments, the first retainer layer 218 and the second retainer layer 220 may be a foam having pore sizes in a range of about 400 microns to about 600 microns. The tensile strength of the first retainer layer 218 and the second retainer layer 220 may also vary according to needs of a prescribed therapy. For example, the tensile strength of a foam may be increased for instillation of topical treatment solutions. The 25% compression load deflection of the first retainer layer 218 and the second retainer layer 220 may be at least 0.35 pounds per square inch, and the 65% compression load deflection may be at least 0.43 pounds per square inch. In some embodiments, the tensile strength of the first retainer layer 218 and the second retainer layer 220 may be at least 10 pounds per square inch. The first retainer layer 218 and the second retainer layer 220 may have a tear strength of at least 2.5 pounds per inch. In one non-limiting example, the first retainer layer 218 and the second retainer layer 220 may each be an open-cell, reticulated polyurethane foam such as V.A.C.® GRANUFOAM™ Dressing available from Kinetic Concepts, Inc. of San Antonio, Texas; in other embodiments the first retainer layer 218 and the second retainer layer 220 may be an open-cell, reticulated polyurethane foam such as a V.A.C. VERAFLO™ dressing, also available from Kinetic Concepts, Inc., of San Antonio, Texas. In other embodiments, the first retainer layer 218 and the second retainer layer 220 may be formed of an un-reticulated open-cell foam.

In some embodiments, the coupling layer 222 may be a layer of coated polyurethane film having a plurality of perforations 234 extending through the coupling layer 222. The film may have a first side coated with a first adhesive and a second side coated with a second adhesive. The film, the first adhesive, and the second adhesive may be perforated to permit fluid communication across the coupling layer 222. The first adhesive may couple the film of the coupling layer 222 to the first retainer layer 218, and the second adhesive may couple the film of the coupling layer 222 to the second retainer layer 220. In some embodiments, the coupling layer 222 may releasably couple the second retainer layer 220 to the first retainer layer 218. For example, the second adhesive may have a higher bond strength than the first adhesive so that, if the second retainer layer 220 is removed from the first retainer layer 218, the film, the first adhesive, and the second adhesive of the coupling layer 222 are removed with the second retainer layer 220.

In some embodiments, the coupling layer 222 may be generally non-adherent material having some tack. For example, the coupling layer 222 may be an open mesh formed from cellulose acetate coated with a soft tack silicone such as ADAPTIC TOUCH™ Non-Adhering Silicone Dressing available from SYSTAGENIX™. In some embodiments, the second retainer layer 220 and the coupling layer 222 may be removed and used on a separate tissue site. In other embodiments, the coupling layer 222 may be a slow release antimicrobial, a humectant similar to honey that is capable of managing moisture and aiding in wound management, or a bioactive delivery slow release chemical component that can be distributed without contacting a surface of a tissue site and/or otherwise attenuating microstrain in the tissue site.

In some embodiments, the first retainer layer 218 may be coupled to the second retainer layer 220 by providing the coupling layer 222 in a roll of material. The roll of adhesive material may be cut into sheets of adhesive material. The sheets of adhesive material may be positioned over and laid onto a layer of the foam material forming the first retainer layer 218. A layer of foam material forming the second retainer layer 220 may be positioned over and laid onto the sheet of activated adhesive material. The assembly of two layers of foam material sandwiching a sheet of adhesive material may then be passed through nip rollers, compressing and curing the assembly. Preferably, the compressive force applied may be less than a compressive force necessary to permanently deform the foam material. The assembly may be then be separated into sub-assemblies each having the first retainer layer 218, the coupling layer 222, and the second retainer layer 220. In some embodiments, the foam material used may be a V.A.C. VERAFLO™ Dressing material.

As illustrated in the example of FIG. 2, in some embodiments, the dressing 104 may include a fluid conductor 250 and a dressing interface 255. As shown in the example of FIG. 2, the fluid conductor 250 may be a flexible tube, which can be fluidly coupled on one end to the dressing interface 255. The dressing interface 255 may be an elbow connector, as shown in the example of FIG. 2, which can be placed over an aperture 260 in the cover 116 to provide a fluid path between the fluid conductor 250 and the tissue interface 114. In some embodiments, the tissue interface 114 may be provided as a portion of an assembly forming the dressing 104. In other embodiments, the tissue interface 114 may be provided separately from the cover 116, the fluid conductor 250, and the dressing interface 255 for assembly of the dressing 104 at the point of use.

Figures 3, 5:
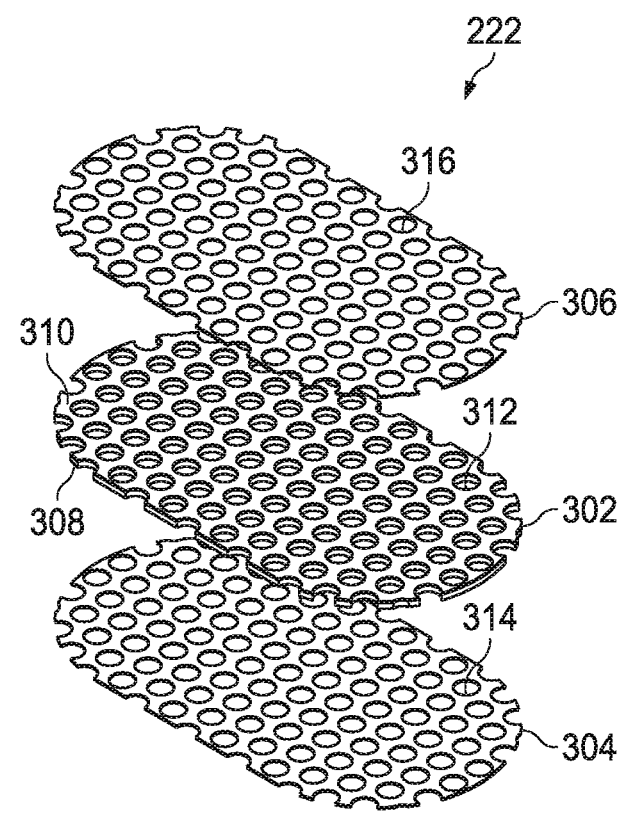
FIG. 3 is an assembly view of a coupling layer of FIG. 2, illustrating additional details that may be associated with some embodiments.
FIG. 5 is a plan view illustrating additional details that may be associated with some embodiments of a hole of the contact layer of FIG. 2.

FIG. 3 is an assembly view of the coupling layer 222, illustrating additional details that may be associated with some embodiments. In some embodiments, the coupling layer 222 may comprise a film layer 302, a first adhesive 304, and a second adhesive 306. The film layer 302 may be a polyurethane film. For example, the film layer 302 may be a film formed from polyurethane, such as polyether polyurethane having a thickness between about 25 microns and about 50 microns and preferably about 40 microns. The film layer 302 may have a first surface 308 and a second surface 310. The first adhesive 304 may be coupled to the first surface 308 of the film layer 302. The first adhesive 304 may have a bond strength of less than about 0.5N/25 mm. The first adhesive 304 may have a coating weight of about 150 g.s.m. The second adhesive 306 may be coupled to the second surface 310 of the film layer 302. The second adhesive 306 may have a bond strength of about 8.0N/25 mm. The second adhesive 306 may have a coating weight of about 40 g.s.m.

The perforations 234 of the coupling layer 222 may comprise separate perforations in each layer of the coupling layer 222. For example, the film layer 302 may have a plurality of perforations 312, the first adhesive 304 may have a plurality of perforations 316, and the second adhesive may have a plurality of perforations 718. Each of the plurality of perforations 312, the plurality of perforations 314, and the plurality of perforations 718 may have an average effective diameter of about 1.6 mm and a pitch of about 0.06 inches. Preferably, the plurality of perforations 312, the plurality of perforations 314, and the plurality of perforations 718 are coincident. In some embodiments, the plurality of perforations 312, the plurality of perforations 314, and the plurality of perforations 718 may be formed by coupling the first adhesive 304 and the second adhesive 306 to the film layer 302 and then forming the plurality of perforations 312, the plurality of perforations 314, and the plurality of perforations 718. In some embodiments, the plurality of perforations 312, the plurality of perforations 314, and the plurality of perforations 718 may be formed by cutting, melting, vaporizing, or otherwise removing material from the film layer 302, the first adhesive 304, and the second adhesive 306. In some embodiments, the coupling layer 222 may be a Vancive Medical MED6501SI Double-Coated, Trilaminate Polyurethane Film with Soft Silicone Adhesive.

The second adhesive 306 may couple the film layer 302 of the coupling layer 222 to the second retainer layer 220, and the first adhesive 304 may couple the film of the coupling layer 222 to the first retainer layer 218. In some embodiments, the second adhesive 306 may have a higher bond strength than the first adhesive 304 so that, if the second retainer layer 220 is removed from the first retainer layer 218, the film layer 302, the first adhesive 304, and the second adhesive 306 of the coupling layer 222 are removed with the second retainer layer 220. In some embodiments, the coupling layer 222 and the second retainer layer 220 may be separated from the first retainer layer 218 and used independently of the remaining tissue interface 114.

Figure 4:
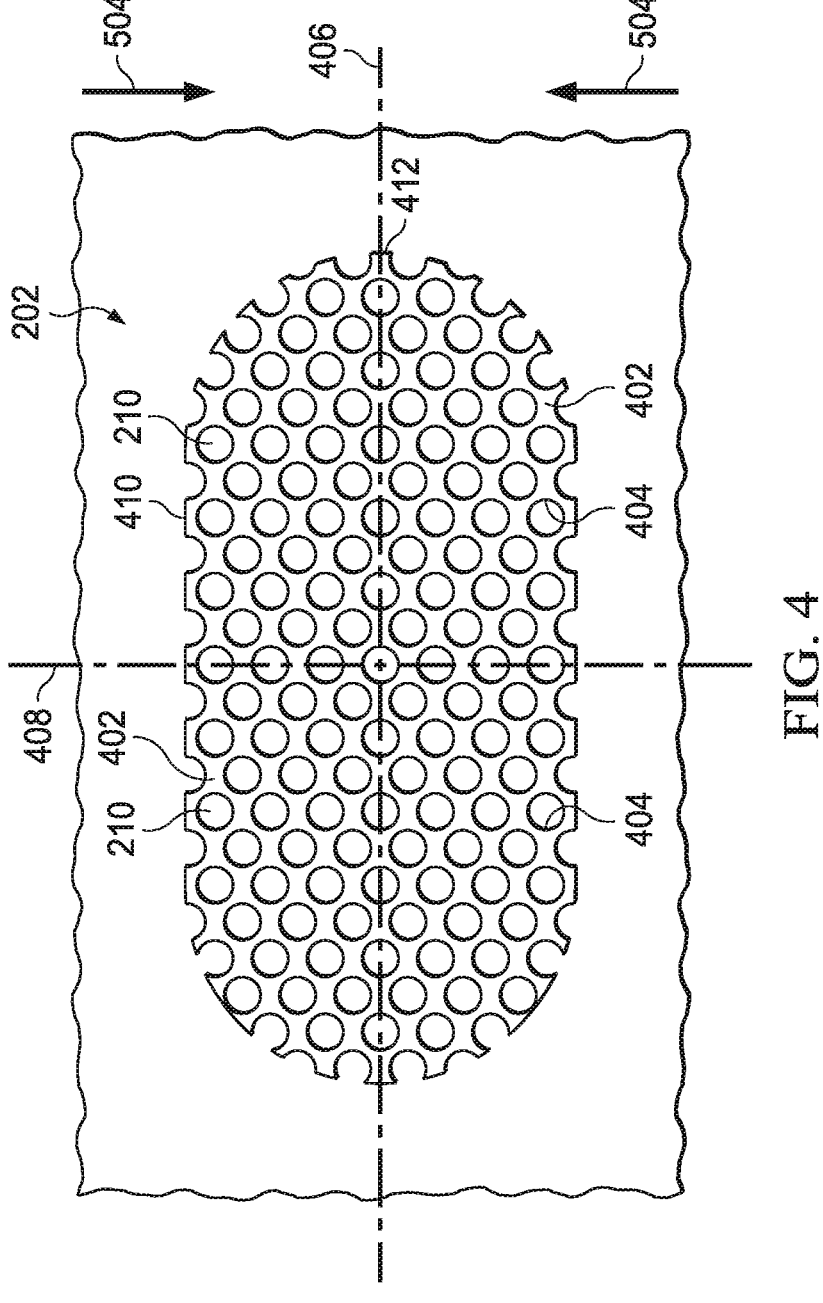
FIG. 4 is a plan view, illustrating additional details that may be associated with some embodiments of a contact layer.

FIG. 4 is a plan view, illustrating additional details that may be associated with some embodiments of the contact layer 202. The contact layer 202 may include the plurality of through-holes 210 or other perforations extending through the contact layer 202 to form walls 402. In some embodiments, an exterior surface of the walls 402 may be parallel to sides of the contact layer 202. In other embodiments, an interior surface of the walls 402 may be generally perpendicular to the second surface 208 and the first surface 206 of the contact layer 202. Generally, the exterior surface or surfaces of the walls 402 may be coincident with the second surface 208 and the first surface 206. The interior surface or surfaces of the walls 402 may form a perimeter 404 of each through-hole 210 and may connect the second surface 208 to the first surface 206. In some embodiments, the through-holes 210 may have a circular shape as shown. In some embodiments, the through-holes 210 may have average effective diameters between about 5 mm and about 20 mm, and in some embodiments, the average effective diameters of the through-holes 210 may be about 10 mm. The through-holes 210 may have a depth that is about equal to the thickness 212 of the contact layer 202. For example, the through-holes 210 may have a depth between about 6 mm to about 10 mm, and more specifically, about 8 mm at ambient pressure.

In some embodiments, the contact layer 202 may have a first orientation line 406 and a second orientation line 408 that is perpendicular to the first orientation line 406. The first orientation line 406 and the second orientation line 408 may be lines of symmetry of the contact layer 202. A line of symmetry may be, for example, an imaginary line across the second surface 208 or the first surface 206 of the contact layer 202 defining a fold line such that if the contact layer 202 is folded on the line of symmetry, the through-holes 210 and the walls 402 on each side would be coincidentally aligned. Generally, the first orientation line 406 and the second orientation line 408 aid in the description of the contact layer 202. In some embodiments, the first orientation line 406 and the second orientation line 408 may be used to refer to the desired directions of contraction of the contact layer 202. For example, the desired direction of contraction may be parallel to the second orientation line 408 and perpendicular to the first orientation line 406. In other embodiments, the desired direction of contraction may be parallel to the first orientation line 406 and perpendicular to the second orientation line 408. In still other embodiments, the desired direction of contraction may be at a non-perpendicular angle to both the first orientation line 406 and the second orientation line 408. In other embodiments, the contact layer 202 may not have a desired direction of contraction.

Generally, the contact layer 202 may be placed at the tissue site so that the second orientation line 408 extends across debris located at the tissue site. Although the contact layer 202 is shown as having a generally ovoid shape including longitudinal edges 410 and circular edges 412, the contact layer 202 may have other shapes. For example, the contact layer 202 may have a rectangular, diamond, square, circular, triangular, or amorphous shape. In some embodiments, the shape of the contact layer 202 may be selected to accommodate the type of tissue site being treated. For example, the contact layer 202 may have an oval or circular shape to accommodate an oval or circular tissue site. The contact layer 202 may be sizeable. For example, the contact layer 202 may be cut, torn, or otherwise separated into portions to permit the contact layer 202 to be diminished in size for smaller tissue sites. In some embodiments, the first orientation line 406 may be parallel to the longitudinal edges 410.

FIG. 5 is a plan view illustrating additional details that may be associated with some embodiments of the through-hole 210 of the contact layer 202 of FIG. 4. In FIG. 5, a single through-hole 210 having a circular shape is shown. The through-hole 210 may include a center 502 and the perimeter 404. The through-hole 210 may have a perforation shape factor (PSF). The perforation shape factor (PSF) may represent an orientation of the through-hole 210 relative to the first orientation line 406 and the second orientation line 408. Generally, the perforation shape factor (PSF) is a ratio of ½ a maximum length of the through-hole 210 that is parallel to the desired direction of contraction to ½ a maximum length of the through-hole 210 that is perpendicular to the desired direction of contraction. For descriptive purposes, the desired direction of contraction is parallel to the second orientation line 408. The desired direction of contraction may be indicated by a lateral force 504. For reference, the through-hole 210 may have an X-axis 506 extending through the center 502 parallel to the first orientation line 406, and a Y-axis 508 extending through the center 502 parallel to the second orientation line 408. The perforation shape factor (PSF) of the through-hole 210 may be defined as a ratio of a line segment 510 on the Y-axis 508 extending from the center 502 to the perimeter 404 of the through-hole 210, to a line segment 512 on the X-axis 506 extending from the center 502 to the perimeter 404 of the through-hole 210. If a length of the line segment 510 is 2.5 mm and the length of the line segment 512 is 2.5 mm, the perforation shape factor (PSF) would be 1. In other embodiments, the through-holes 210 may have other shapes and orientations, for example, oval, hexagonal, square, triangular, or amorphous or irregular and be oriented relative to the first orientation line 406 and the second orientation line 408 so that the perforation shape factor (PSF) may range from about 0.5 to about 1.10.

Figure 6:
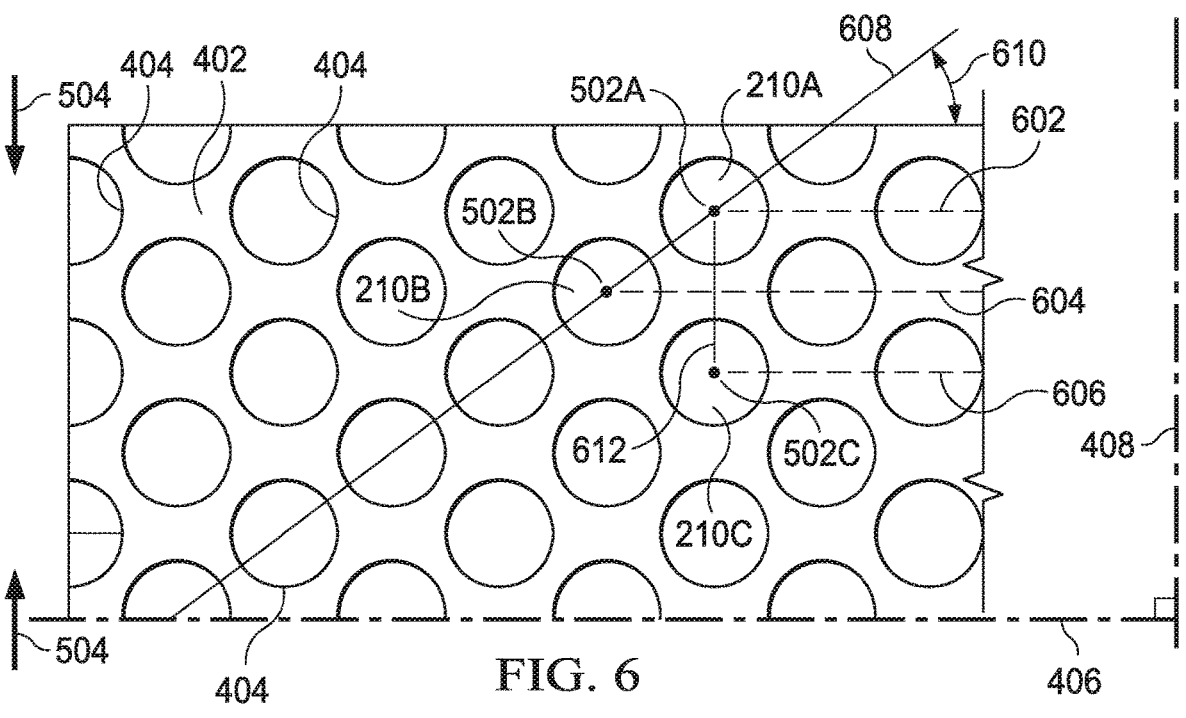
FIG. 6 is a plan view illustrating additional details of a portion of the contact layer of FIG. 2.

FIG. 6 is a plan view illustrating additional details of a portion of the contact layer 202 of FIG. 4. The contact layer 202 may include the plurality of through-holes 210 aligned in parallel rows to form an array. The array of through-holes 210 may include a first row 602 of the through-holes 210, a second row 604 of the through-holes 210, and a third row 606 of the through-holes 210. In some embodiments, a width of the wall 402 between the perimeters 404 of adjacent through-holes 210 in a row, such as the first row 602, may be about 5 mm. The centers 502 of the through-holes 210 in adjacent rows, for example, the first row 602 and the second row 604, may be characterized by being offset from the second orientation line 408 along the first orientation line 406. In some embodiments, a line connecting the centers of adjacent rows may form a strut angle (SA) with the first orientation line 406. For example, a first through-hole 210A in the first row 602 may have a center 502A, and a second through-hole 210B in the second row 604 may have a center 502B. A strut line 608 may connect the center 502A with the center 502B. The strut line 608 may form an angle 610 with the first orientation line 406. The angle 610 may be the strut angle (SA) of the contact layer 202. In some embodiments, the strut angle (SA) may be less than about 90°. In other embodiments, the strut angle (SA) may be between about 30° and about 70° relative to the first orientation line 406. In other embodiments, the strut angle (SA) may be about 66° from the first orientation line 406. Generally, as the strut angle (SA) decreases, a stiffness of the contact layer 202 in a direction parallel to the first orientation line 406 may increase. Increasing the stiffness of the contact layer 202 parallel to the first orientation line 406 may increase the compressibility of the contact layer 202 perpendicular to the first orientation line 406. Consequently, if negative pressure is applied to the contact layer 202, the contact layer 202 may be more compliant or compressible in a direction perpendicular to the first orientation line 406. By increasing the compressibility of the contact layer 202 in a direction perpendicular to the first orientation line 406, the contact layer 202 may collapse to apply the lateral force 504 to the tissue site as described in more detail below.

In some embodiments, the centers 502 of the through-holes 210 in alternating rows, for example, the center 502A of the first through-hole 210A in the first row 602 and a center 502C of a through-hole 210C in the third row 606, may be spaced from each other parallel to the second orientation line 408 by a length 612. In some embodiments, the length 612 may be greater than an effective diameter of the through-hole 210. If the centers 502 of through-holes 210 in alternating rows are separated by the length 612, the exterior surface of the walls 402 parallel to the first orientation line 406 may be considered continuous. Generally, the exterior surface of the walls 402 may be continuous if the exterior surface of the walls 402 do not have any discontinuities or breaks between through-holes 210. In some embodiments, the length 612 may be between about 7 mm and about 25 mm.

Regardless of the shape of the through-holes 210, the through-holes 210 in the contact layer 202 may leave void spaces in the contact layer 202 and on the second surface 208 and the first surface 206 of the contact layer 202 so that only the exterior surface of the walls 402 of the contact layer 202 remain with a surface available to contact the tissue site. It may be desirable to minimize the exterior surface of the walls 402 so that the through-holes 210 may collapse, causing the contact layer 202 to collapse and generate the lateral force 504 in a direction perpendicular to the first orientation line 406. However, it may also be desirable not to minimize the exterior surface of the walls 402 so much that the contact layer 202 becomes too fragile for sustaining the application of a negative pressure. The void space percentage (VS) of the through-holes 210 may be equal to the percentage of the volume or surface area of the void spaces of the second surface 208 created by the through-holes 210 to the total volume or surface area of the second surface 208 of the contact layer 202. In some embodiments, the void space percentage (VS) may be between about 40% and about 75%. In other embodiments, the void space percentage (VS) may be about 55%. The organization of the through-holes 210 can also impact the void space percentage (VS), influencing the total surface area of the contact layer 202 that may contact the tissue site. In some embodiments, the longitudinal edge 410 and the circular edge 412 of the contact layer 202 may be discontinuous. An edge may be discontinuous where the through-holes 210 overlap an edge causing the edge to have a non-linear profile. A discontinuous edge may reduce the disruption of keratinocyte migration and enhance re-epithelialization while negative pressure is applied to the dressing 104.

In some embodiments, the through-holes 210 may be formed during molding of the contact layer 202. In other embodiments, the through-holes 210 may be formed by cutting, melting, drilling, or vaporizing the contact layer 202 after the contact layer 202 is formed. For example, the through-holes 210 may be formed in the contact layer 202 by laser cutting the compressed foam of the contact layer 202. In some embodiments, the through-holes 210 may be formed so that the interior surfaces of the walls 402 of the through-holes 210 are parallel to the thickness 212. In other embodiments, the through-holes 210 may be formed so that the interior surfaces of the walls 402 of the through-holes 210 form a non-perpendicular angle with the second surface 208. In still other embodiments, the interior surfaces of the walls 402 of the through-holes 210 may taper toward the center 502 of the through-holes 210 to form conical, pyramidal, or other irregular through-hole shapes. If the interior surfaces of the walls 402 of the through-holes 210 taper, the through-holes 210 may have a height less than the thickness 212 of the contact layer 202.

In some embodiments, formation of the through-holes 210 may thermoform the material of the contact layer 202, for example a compressed foam or a felted foam, causing the interior surface of the walls 402 extending between the second surface 208 and the first surface 206 to be smooth. As used herein, smoothness may refer to the formation of the through-holes 210 that causes the interior surface of the walls 402 that extends between the second surface 208 and the first surface 206 to be substantially free of pores if compared to an uncut portion of the contact layer 202. For example, laser-cutting the through-holes 210 into the contact layer 202, may plastically deform the material of the contact layer 202, closing any pores on the interior surfaces of the walls 402 that extend between the second surface 208 and the first surface 206. In some embodiments, a smooth interior surface of the walls 402 may limit or otherwise inhibit ingrowth of tissue into the contact layer 202 through the through-holes 210. In other embodiments, the smooth interior surfaces of the walls 402 may be formed by a smooth material or a smooth coating.

In some embodiments, an effective diameter of the through-holes 210 may be selected to permit flow of particulates through the through-holes 210. In some embodiments, the diameter of the through-holes 210 may be selected based on the size of the solubilized debris to be lifted from the tissue site. Larger through-holes 210 may allow larger debris to pass through the contact layer 202, and smaller through-holes 210 may allow smaller debris to pass through the contact layer 202 while blocking debris larger than the through-holes. In some embodiments, successive applications of the dressing 104 can use contact layers 202 having successively smaller diameters of the through-holes 210 as the size of the solubilized debris in the tissue site decreases. Sequentially decreasing diameters of the through-holes 210 may also aid in fine tuning a level of tissue disruption to the debris during the treatment of the tissue site. The diameter of the through-holes 210 can also influence fluid movement in the contact layer 202 and the dressing 104. For example, the contact layer 202 can channel fluid in the dressing 104 toward the through-holes 210 to aid in the disruption of the debris on the tissue site. Variation of the diameters of the through-holes 210 can vary how fluid is moved through the dressing 104 with respect to both the removal of fluid and the application of negative pressure. In some embodiments, the diameter of the through-holes 210 is between about 5 mm and about 20 mm and, more specifically, about 10 mm.

An effective diameter of a non-circular area is defined as a diameter of a circular area having the same surface area as the non-circular area. In some embodiments, each through-hole 210 may have an effective diameter of about 3.5 mm. In other embodiments, each through-hole 210 may have an effective diameter between about 5 mm and about 20 mm. The effective diameter of the through-holes 210 should be distinguished from the porosity of the material forming the walls 402 of the contact layer 202. Generally, an effective diameter of the through-holes 210 is an order of magnitude larger than the effective diameter of the pores of a material forming the contact layer 202. For example, the effective diameter of the through-holes 210 may be larger than about 1 mm, while the walls 402 may be formed from V.A.C.® GRANUFOAM™ Dressing having a pore size less than about 600 microns. In some embodiments, the pores of the walls 402 may not create openings that extend all the way through the material. Generally, the through-holes 210 do not include pores formed by the foam formation process, and the through-holes 210 may have an average effective diameter that is greater than ten times an average effective diameter of pores of a material.

Referring now to both FIG. 4 and FIG. 6, the through-holes 210 may form a pattern depending on the geometry of the through-holes 210 and the alignment of the through-holes 210 between adjacent and alternating rows in the contact layer 202 with respect to the first orientation line 406. If the contact layer 202 is subjected to negative pressure, the through-holes 210 of the contact layer 202 may contract. As used herein, contraction can refer to both vertical compression of a body parallel to a thickness of the body, such as the contact layer 202, and lateral compression of a body perpendicular to a thickness of the body, such as the contact layer 202. In some embodiments the void space percentage (VS), the perforation shape factor (PSF), and the strut angle (SA) may cause the contact layer 202 to contract along the second orientation line 408 perpendicular to the first orientation line 406 as shown in more detail in FIG. 7.

Figure 7:
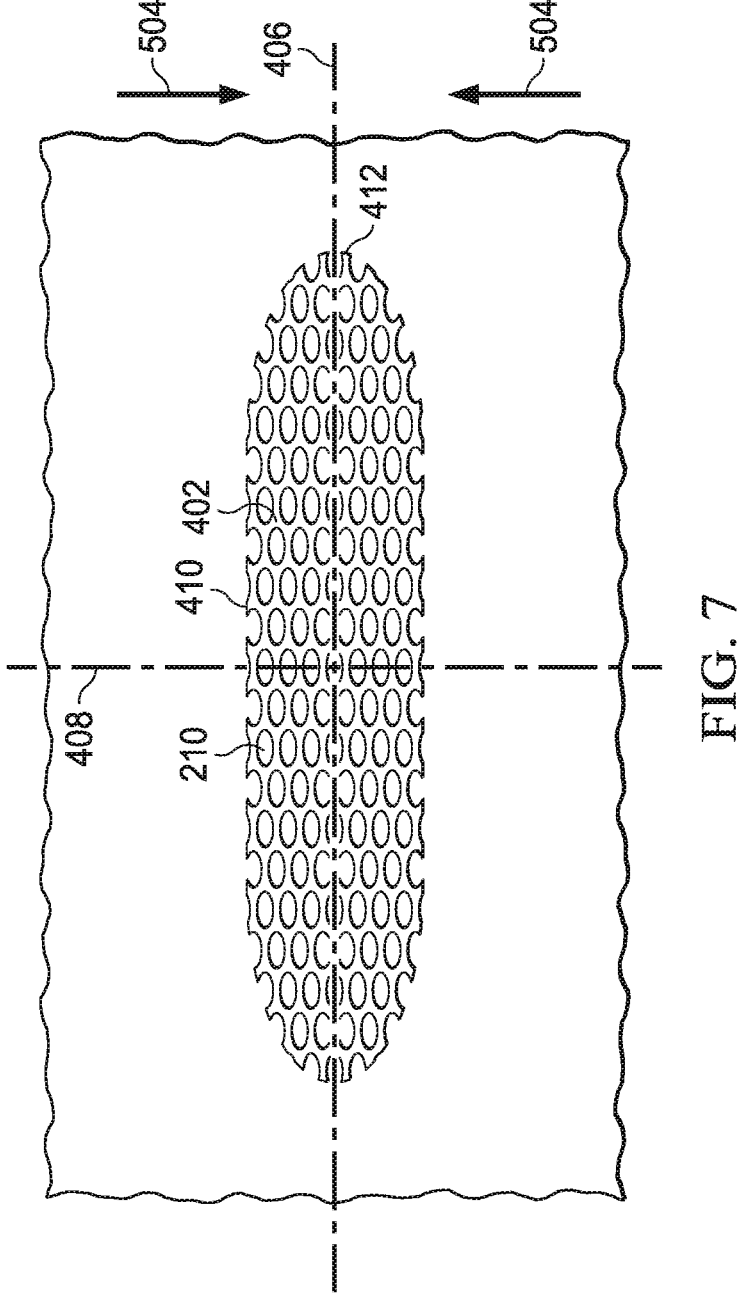
FIG. 7 is a plan view illustrating additional details of the tissue interface of FIG. 2 in a contracted state.

FIG. 7 is a plan view illustrating additional details of the contact layer 202 of FIG. 4 in a contracted state. If the contact layer 202 is positioned on the tissue site, the contact layer 202 may generate the lateral force 504 along the second orientation line 408, contracting the contact layer 202, as shown in more detail in FIG. 7. The lateral force 504 may be optimized by adjusting the factors described above as set forth in Table 1 below. In some embodiments, the through-holes 210 may be circular, have a strut angle (SA) of approximately 37°, a void space percentage (VS) of about 54%, a firmness factor (FF) of about 5, a perforation shape factor (PSF) of about 1, and a diameter of about 5 mm. If the contact layer 202 is subjected to a negative pressure of about −125 mm Hg, the lateral force 504 generated by the contact layer 202 is approximately 11.9 N. If the diameter of the through-holes 210 of the contact layer 202 is increased to about 20 mm, the void space percentage (VS) changed to about 52%, the strut angle (SA) changed to about 52°, and the perforation shape factor (PSF) and the firmness factor (FF) remain the same, the lateral force 504 is decreased to about 6.5 N. In other embodiments, the through-holes 210 may be hexagonal, have a strut angle (SA) of approximately 66°, a void space percentage (VS) of about 55%, a firmness factor (FF) of about 5, a perforation shape factor (PSF) of about 1.07, and an effective diameter of about 5 mm. If the contact layer 202 is subjected to a negative pressure of about −125 mm Hg, the lateral force 504 generated by the contact layer 202 is approximately 13.3 N. If the effective diameter of the through-holes 210 of the contact layer 202 is increased to 10 mm, the lateral force 504 is decreased to about 7.5 N.

As illustrated in FIG. 7, the contact layer 202 is in the second position, or contracted position, as indicated by the lateral force 504. In operation, negative pressure is supplied to the sealed environment with the negative-pressure source 102. In response to the supply of negative pressure, the contact layer 202 contracts from the relaxed position illustrated in FIG. 4 to the contracted position illustrated in FIG. 7. In some embodiments, the thickness 212 of the contact layer 202 remains substantially the same. When the negative pressure is removed, for example, by venting the negative pressure from the sealed space, the contact layer 202 expands back to the relaxed position. If the contact layer 202 is cycled between the contracted and relaxed positions of FIG. 6 and FIG. 4, respectively, the second surface 208 of the contact layer 202 may disrupt the debris on the tissue site by rubbing the debris from the tissue site. The edges of the through-holes 210 formed by the second surface 208 and the interior surfaces or transverse surfaces of the walls 402 can form cutting edges that can disrupt the debris in the tissue site, allowing the debris to exit through the through-holes 210. In some embodiments, the cutting edges are defined by the perimeter 404 where each through-hole 210 intersects the second surface 208.

In some embodiments, the material, the void space percentage (VS), the firmness factor, the strut angle, the hole shape, the perforation shape factor (PSF), and the hole diameter may be selected to increase compression or collapse of the contact layer 202 in a lateral direction, as shown by the lateral force 504, by forming weaker walls 402. Conversely, the factors may be selected to decrease compression or collapse of the contact layer 202 in a lateral direction, as shown by the lateral force 504, by forming stronger walls 402. Similarly, the factors described herein can be selected to decrease or increase the compression or collapse of the contact layer 202 perpendicular to the lateral force 504.

In some embodiments, the therapy system 100 may provide cyclic therapy. Cyclic therapy may alternately apply negative pressure to and vent negative pressure from a sealed space or sealed environment containing the tissue interface 114. In some embodiments, negative pressure may be supplied to the tissue site until the pressure in the sealed environment reaches a predetermined therapy pressure. If negative pressure is supplied to the sealed environment, the debris and the subcutaneous tissue underlying the debris may be drawn into the through-holes 210. In some embodiments, the sealed environment may remain at the therapy pressure for a predetermined therapy period such as, for example, about 10 minutes. In other embodiments, the therapy period may be longer or shorter as needed to supply appropriate negative-pressure therapy to the tissue site.

Following the therapy period, the sealed environment may be vented. For example, the negative-pressure source 102 may fluidly couple the sealed environment to the atmosphere (not shown), allowing the sealed environment to return to ambient pressure. In some embodiments, the negative-pressure source 102 may vent the sealed environment for about 1 minute. In other embodiments, the negative-pressure source 102 may vent the sealed environment for longer or shorter periods. After venting of the sealed environment, the negative-pressure source 102 may be operated to begin another negative-pressure therapy cycle.

In some embodiments, instillation therapy may be combined with negative-pressure therapy. For example, following the therapy period of negative-pressure therapy, the solution source 118 may operate to provide fluid to the sealed environment. In some embodiments, the solution source 118 may provide fluid while the negative-pressure source 102 vents the sealed environment. For example, the positive-pressure source 120 may be configured to move instillation fluid from the solution source 118 to the sealed environment. In some embodiments, the solution source 118 may not have a pump and may operate using a gravity feed system. In other embodiments, the negative-pressure source 102 may not vent the sealed environment. Instead, the negative pressure in the sealed environment is used to draw instillation fluid from the solution source 118 into the sealed environment.

In some embodiments, the solution source 118 may provide a volume of fluid to the sealed environment. In some embodiments, the volume of fluid may be the same as a volume of the sealed environment. In other embodiments, the volume of fluid may be smaller or larger than the sealed environment as needed to appropriately apply instillation therapy. Instilling of the tissue site may raise a pressure in the sealed environment to a pressure greater than the ambient pressure, for example to between about 0 mm Hg and about 15 mm Hg and, more specifically, about 5 mm Hg. In some embodiments, the fluid provided by the solution source 118 may remain in the sealed environment for a dwell time. In some embodiments, the dwell time is about 5 minutes. In other embodiments, the dwell time may be longer or shorter as needed to appropriately administer instillation therapy to the tissue site. For example, the dwell time may be zero.

At the conclusion of the dwell time, the negative-pressure source 102 may be operated to draw the instillation fluid into the container, completing a cycle of therapy. As the instillation fluid is removed from the sealed environment with negative pressure, negative pressure may also be supplied to the sealed environment, starting another cycle of therapy.

Figure 8:
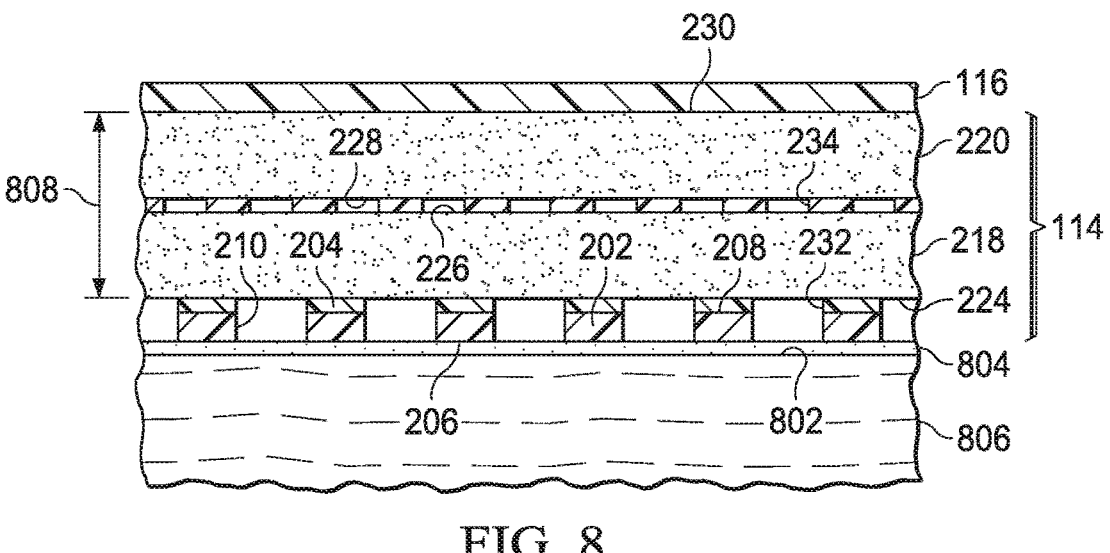
FIG. 8 is a sectional view of a portion of the tissue interface of FIG. 2, illustrating additional details that may be associated with some embodiments.

FIG. 8 is a sectional view of a portion of the tissue interface 114, illustrating additional details that may be associated with some embodiments. The contact layer 202, the adhesive layer 204, the first retainer layer 218, the coupling layer 222, and the second retainer layer 220 may be placed at a tissue site 802 having the debris 804 covering the subcutaneous tissue 806. The adhesive layer 204 can be coupled to the second surface 208 of the contact layer 202 and the first surface 224 of the first retainer layer 218. The coupling layer 222 may be coupled to the second surface 226 of the first retainer layer 218 and the first surface 228 of the second retainer layer 220. For example, a clinician may place the tissue interface 114 having the contact layer 202, the adhesive layer 204, the first retainer layer 218, the coupling layer 222, and the second retainer layer 220 at the tissue site 802. In some embodiments, the tissue interface 114 may be packaged in a sterile container that the clinician may open and remove. The tissue interface 114 having the contact layer 202, the adhesive layer 204, the first retainer layer 218, the coupling layer 222, and the second retainer layer 220 may be removed as a single piece for placement at the tissue site 802.

In some embodiments, the tissue interface 114 may have a length and width that is greater than an opening of the tissue site 802. The tissue interface 114 may be sized to permit the tissue interface 114 to be passed through the opening of the tissue site 802 to be placed adjacent to the debris 804. Sizing can include removing a portion of the tissue interface 114, for example, by cutting, tearing, melting, dissolving, vaporizing, or otherwise separating a portion of the tissue interface 114 from remaining portions of the tissue interface 114. During sizing of the tissue interface 114, the contact layer 202, the adhesive layer 204, the first retainer layer 218, the coupling layer 222, and the second retainer layer 220 may be sized at substantially the same time. For example, the coupling of the contact layer 202 to the first retainer layer 218 by the adhesive layer 204, and the first retainer layer 218 to the second retainer layer 220 by the coupling layer 222 can permit the tissue interface 114 to be cut by cutting through all layers simultaneously by, for example, using scissors.

Following sizing and initial placement of the tissue interface 114 at the tissue site 802, the cover 116 may be placed over the second retainer layer 220 to provide a sealed environment for the application of negative-pressure therapy or instillation therapy. In some embodiments, the tissue interface 114 may have a total thickness that is greater than a depth of the tissue site 802. The second retainer layer 220 may be removed from the first retainer layer 218 to decrease the total thickness of the tissue interface 114 to a depth that is closer in approximation to the depth of the tissue site 802. For example, the second retainer layer 220 may be peeled from the first retainer layer 218; the coupling layer 222 having the second adhesive 306 with a stronger bond strength coupled to the second retainer layer 220 may separate from the first retainer layer 218 and remain with the second retainer layer 220. As shown in FIG. 8, the first retainer layer 218 and the second retainer layer 220 may have a thickness 808 if the pressure in the sealed environment is about an ambient pressure. In some embodiments, the thickness 808 may be about 16 mm. In other embodiments, for example, where the second retainer layer 220 is removed from the tissue interface 114, the thickness 808 may be about 8 mm.

Figure 9:
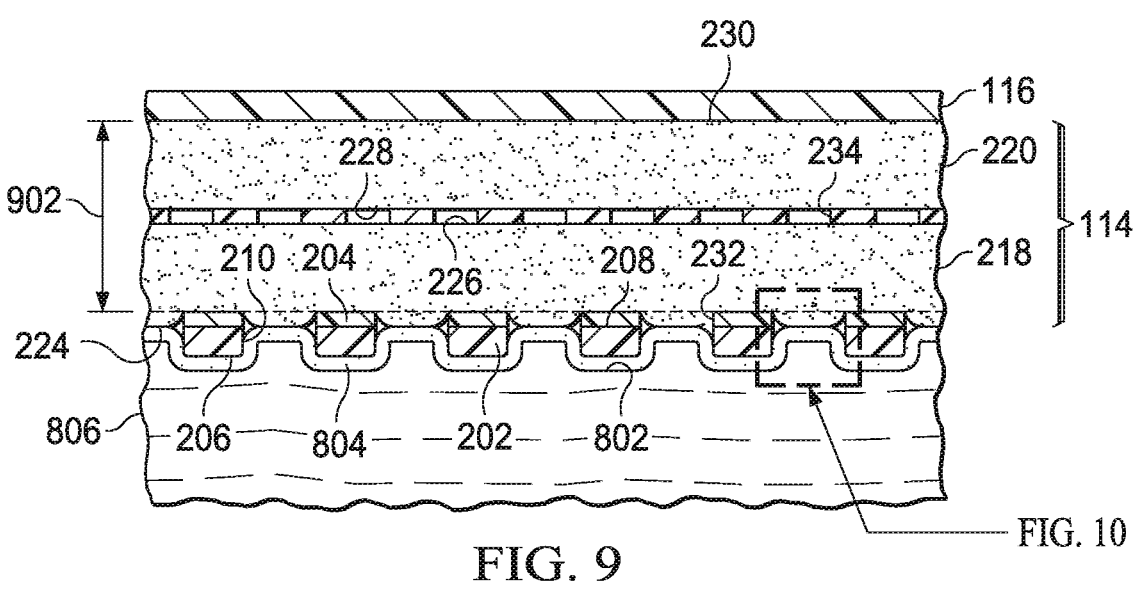
FIG. 9 is a sectional view of the tissue interface of FIG. 2 during negative-pressure therapy, illustrating additional details that may be associated with some embodiments.

FIG. 9 is a sectional view of a portion of the dressing 104 during negative-pressure therapy, illustrating additional details that may be associated with some embodiments. For example, FIG. 9 may illustrate a moment in time where a pressure in the sealed environment may be about −125 mm Hg of negative pressure. In some embodiments, the first retainer layer 218 and the second retainer layer 220 may be a non-felted foam, and the contact layer 202 may be a felted foam. In response to the application of negative pressure, the contact layer 202 may not compress, the first retainer layer 218, and the second retainer layer 220 may compress so that the first retainer layer 218, the coupling layer 222, and the second retainer layer 220 have a thickness 902. In some embodiments, the thickness 902 of the first retainer layer 218, the coupling layer 222, and the second retainer layer 220 during negative-pressure therapy may be less than the thickness 808 of the first retainer layer 218, the coupling layer 222, and the second retainer layer 220 if the pressure in the sealed environment is about the ambient pressure.

In some embodiments, negative pressure in the sealed environment can generate concentrated stresses in the first retainer layer 218 adjacent to the through-holes 210 in the contact layer 202. The concentrated stresses can cause macro-deformation of the first retainer layer 218 that draws portions of the first retainer layer 218 into the through-holes 210 of the contact layer 202. Similarly, negative pressure in the sealed environment can generate concentrated stresses in the debris 804 adjacent to the through-holes 210 in the contact layer 202. The concentrated stresses can cause macro-deformations of the debris 804 and the subcutaneous tissue 806 that draws portions of the debris 804 and the subcutaneous tissue 806 into the through-holes 210.

Figure 10:
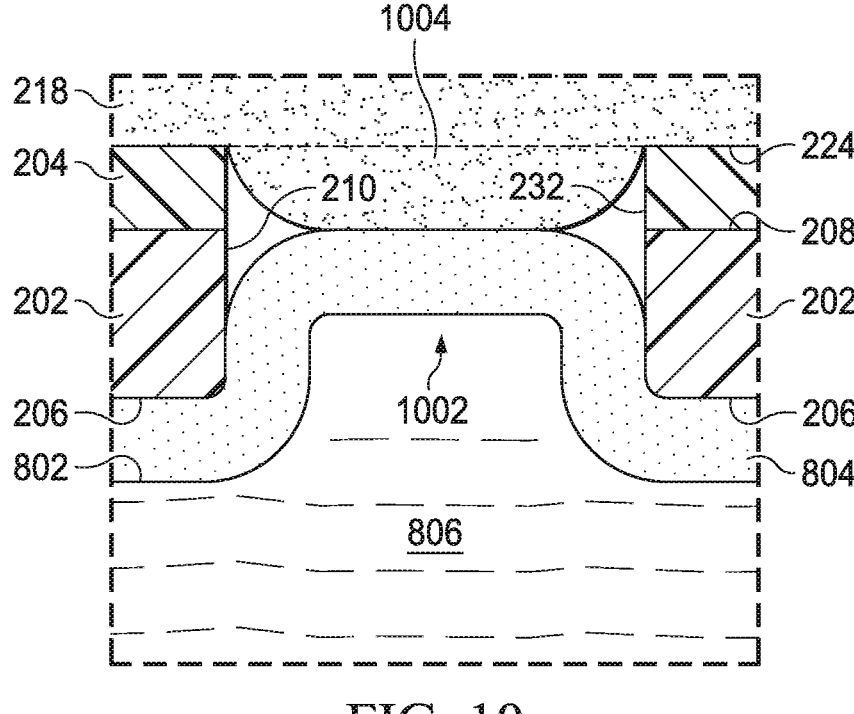
FIG. 10 is a detail view of a portion of the tissue interface of FIG. 9, illustrating additional details of the operation of the tissue interface during negative-pressure therapy.

FIG. 10 is a detail view of the contact layer 202 and a portion of the first retainer layer 218, illustrating additional details of the operation of the contact layer 202, the first retainer layer 218, and the second retainer layer 220 during negative-pressure therapy. The through-holes 210 of the contact layer 202 may create macro-pressure points in portions of the debris 804, and the subcutaneous tissue 806 that are in contact with the second surface 208 of the contact layer 202, causing tissue puckering and nodules 1002 in the debris 804 and the subcutaneous tissue 806.

A height of the nodules 1002 over the surrounding tissue may be selected to maximize disruption of debris 804 and minimize damage to subcutaneous tissue 806 or other desired tissue. Generally, the pressure in the sealed environment can exert a force that is proportional to the area over which the pressure is applied. At the through-holes 210 of the contact layer 202, the force may be concentrated as the resistance to the application of the pressure is less than in the walls 402 of the contact layer 202. In response to the force generated by the pressure at the through-holes 210, the debris 804 and the subcutaneous tissue 806 that forms the nodules 1002 may be drawn into and through the through-holes 210 until the force applied by the pressure is equalized by the reactive force of the adhesive layer 204, the debris 804, and the subcutaneous tissue 806. In some embodiments where the negative pressure in the sealed environment may cause tearing, the thickness 212 of the contact layer 202 may be selected to limit the height of the nodules 1002 over the surrounding tissue. In some embodiments, the height of the nodules 1002 may be limited to a height that is less than the thickness 212 of the contact layer 202. In an exemplary embodiment, the thickness 212 of the contact layer 202 may be about 7 mm. During the application of negative pressure, the height of the nodules 1002 may be limited to about 2 mm to about 7 mm. By controlling the height of the nodules 1002 by controlling the thickness 212 of the contact layer 202, the aggressiveness of disruption to the debris 804 and tearing can be controlled.

In some embodiments, the height of the nodules 1002 can also be controlled by controlling an expected compression of the contact layer 202 during negative-pressure therapy. For example, the contact layer 202 may have a thickness 212 of about 8 mm. If the contact layer 202 is formed from a compressed foam, the firmness factor of the contact layer 202 may be higher; however, the contact layer 202 may still reduce in thickness in response to negative pressure in the sealed environment. In one embodiment, application of negative pressure of between about −50 mm Hg and about −350 mm Hg, between about −100 mm Hg and about −250 mm Hg and, more specifically, about −125 mm Hg in the sealed environment may reduce the thickness 212 of the contact layer 202 from about 8 mm to about 3 mm. The height of the nodules 1002 may be limited to be no greater than the thickness 212 of the contact layer 202 during negative-pressure therapy, for example, about 3 mm. By controlling the height of the nodules 1002, the forces applied to the debris 804 by the contact layer 202 can be adjusted and the degree that the debris 804 is stretched can be varied.

In some embodiments, the formation of the nodules 1002 can cause the debris 804 to remain in contact with a tissue interface 114 during negative pressure therapy. For example, the nodules 1002 may contact the sidewalls of the through-holes 210 of the contact layer 202. In some embodiments, formation of the nodules 1002 may lift debris 804 and particulates off of the surrounding tissue, operating in a piston-like manner to move debris 804 toward the first retainer layer 218 and out of the sealed environment.

Portions of the first retainer layer 218 in contact with the first surface 206 of the contact layer 202 may be drawn into the through-holes 210 to form bosses 1004. The bosses 1004 may have a shape that corresponds to the through-holes 210. A height of the bosses 1004 from the first retainer layer 218 may be dependent on the pressure of the negative pressure in the sealed environment, the area of the through-holes 210, and the firmness factor of the first retainer layer 218.

In some embodiments, the first retainer layer 218 may limit the height of the nodules 1002 to the thickness 212 of the contact layer 202 under negative pressure. In other embodiments, the bosses 1004 of the first retainer layer 218 may limit the height of the nodules 1002 to a height that is less than the thickness 212 of the contact layer 202. By controlling the firmness factor of the first retainer layer 218, the height of the bosses 1004 over the surrounding material of the first retainer layer 218 can be controlled. The height of the nodules 1002 can be limited to the difference of the thickness 212 of the contact layer 202 and the height of the bosses 1004. In some embodiments, the height of the bosses 1004 can vary from zero to several millimeters as the firmness factor of the first retainer layer 218 decreases. In an exemplary embodiment, the thickness 212 of the contact layer 202 may be about 7 mm. During the application of negative pressure, the bosses 1004 may have a height between about 4 mm to about 5 mm, limiting the height of the nodules to about 2 mm to about 3 mm. By controlling the height of the nodules 1002 by controlling the thickness 212 of the contact layer 202, the firmness factor of the first retainer layer 218, or both, the aggressiveness of disruption to the debris 804 and tearing can be controlled.

In response to the return of the sealed environment to ambient pressure by venting the sealed environment, the nodules 1002 and the bosses 1004 may leave the through-holes 210, returning to the position shown in FIG. 8. In some embodiments, repeated application of negative-pressure therapy and instillation therapy while the contact layer 202 is disposed over the debris 804 may disrupt the debris 804, allowing the debris 804 to be removed during dressing changes. In other embodiments, the contact layer 202 may disrupt the debris 804 so that the debris 804 can be removed by negative pressure. In still other embodiments, the contact layer 202 may disrupt the debris 804, aiding removal of the debris 804 during debridement processes. With each cycle of therapy, the contact layer 202 may form nodules 1002 in the debris 804. The formation of the nodules 1002 and release of the nodules 1002 by the contact layer 202 during therapy may disrupt the debris. With each subsequent cycle of therapy, disruption of the debris 804 can be increased.

Disruption of the debris 804 can be caused, at least in part, by the concentrated forces applied to the debris 804 by the through-holes 210 and the walls 402 of the contact layer 202. The forces applied to the debris 804 can be a function of the negative pressure supplied to the sealed environment and the area of each through-hole 210. For example, if the negative pressure supplied to the sealed environment is about −125 mm Hg and the diameter of each through-hole 210 is about 5 mm, the force applied at each through-hole 210 is about 0.07 lbs. If the diameter of each through-hole 210 is increased to about 8 mm, the force applied at each through-hole 210 can increase up to 6 times. Generally, the relationship between the diameter of each through-hole 210 and the applied force at each through-hole 210 is not linear and can increase exponentially with an increase in diameter.

In some embodiments, the negative pressure applied by the negative-pressure source 102 may be cycled rapidly. For example, negative pressure may be supplied for a few seconds, then vented for a few seconds, causing a pulsation of negative pressure in the sealed environment. The pulsation of the negative pressure can pulsate the nodules 1002, causing further disruption of the debris 804.

In some embodiments, the cyclical application of instillation therapy and negative pressure therapy may cause micro-floating. For example, negative pressure may be applied to the sealed environment during a negative-pressure therapy cycle. Following the conclusion of the negative-pressure therapy cycle, instillation fluid may be supplied during the instillation therapy cycle. The instillation fluid may cause the contact layer 202 to float relative to the debris. As the contact layer 202 floats, it may change position relative to the position the contact layer 202 occupied during the negative-pressure therapy cycle. The position change may cause the contact layer 202 to engage a slightly different portion of the debris 804 during the next negative-pressure therapy cycle, aiding disruption of the debris 804 and the application of antimicrobial/antibacterial agents by the adhesive layer 204.

The through-holes 210 of the contact layer 202 may generate concentrated stresses that influence disruption of the debris in different ways. For example, different shapes of the through-holes 210 may also focus the stresses generated by the contact layer 202 in advantageous areas. A lateral force, such as the lateral force 504, generated by a contact layer, such as the contact layer 202, may be related to a compressive force generated by applying negative pressure at a therapy pressure to a sealed therapeutic environment. For example, the lateral force 504 may be proportional to a product of a therapy pressure (TP) in the sealed environment, the compressibility factor (CF) of the contact layer 202, and a surface area (A) the second surface 208 of the contact layer 202. The relationship is expressed as follows:

$$\text{Lateral force } \alpha (TP*CF*A)$$

In some embodiments, the therapy pressure TP is measured in $N/m^2$, the compressibility factor (CF) is dimensionless, the area (A) is measured in $m^2$, and the lateral force is measured in Newtons (N). The compressibility factor (CF) resulting from the application of negative pressure to a contact layer may be, for example, a dimensionless number that is proportional to the product of the void space percentage (VS) of a contact layer, the firmness factor (FF) of the contact layer, the strut angle (SA) of the through-holes in the contact layer, and the perforation shape factor (PSF) of the through-holes in the contact layer. The relationship is expressed as follows:

$$\text{Compressibility Factor}(CF) \alpha (VS*FF*\sin(SA)*PSF)$$

Based on the above formulas, contact layers formed from different materials with through-holes of different shapes were manufactured and tested to determine the lateral force of the contact layers. For each contact layer, the therapy pressure TP was about −125 mm Hg and the dimensions of the contact layer were about 200 mm by about 53 mm so that the surface area (A) of the tissue-facing surface of the contact layer was about 106 $cm^2$ or 0.0106 $m^2$. Based on the two equations described above, the lateral force for a Supracor® contact layer 202 having a firmness factor (FF) of 3 was about 13.3 where the Supracor® contact layer 202 had hexagonal through-holes 210 with a distance between opposite vertices of 5 mm, a perforation shape factor (PSF) of 1.07, a strut angle (SA) of approximately 66°, and a void space percentage (VS) of about 55%. A similarly dimensioned V.A.C.® GRANUFOAM™ Dressing contact layer 202 generated the lateral force 504 of about 9.1 Newtons (N).

TABLE 1

| Material | VS | FF | SA | Hole Shape | PSF | Major diam. (mm) | Lateral force |
|---|---|---|---|---|---|---|---|
| V.A.C. ® GRANUFOAM™ Dressing | 56 | 5 | 47 | Ovular | 1 | 10 | 13.5 |
| Supracor ® | 55 | 3 | 66 | Hexagon | 1.1 | 5 | 13.3 |
| V.A.C. ® GRANUFOAM™ Dressing | 40 | 5 | 63 | Triangle | 1.1 | 10 | 12.2 |
| V.A.C. ® GRANUFOAM™ Dressing | 54 | 5 | 37 | Circular | 1 | 5 | 11.9 |
| V.A.C. ® GRANUFOAM™ Dressing | 52 | 5 | 37 | Circular | 1 | 20 | 10.3 |
| Grey Foam | N/A | 5 | N/A | Horizontal stripes | N/A | N/A | 9.2 |
| V.A.C. ® GRANUFOAM™ Dressing | 55 | 5 | 66 | Hexagon | 1.1 | 5 | 9.1 |
| V.A.C. ® GRANUFOAM™ Dressing | N/A | 5 | N/A | Horizontal stripes | N/A | N/A | 8.8 |
| Zotefoam | 52 | 3 | 37 | Circular | 1 | 10 | 8.4 |
| V.A.C. ® GRANUFOAM™ Dressing | 52 | 5 | 37 | Circular | 1 | 10 | 8.0 |
| V.A.C. ® GRANUFOAM™ Dressing | 52 | 5 | 64 | Circular | 1 | 10 | 7.7 |
| V.A.C. ® GRANUFOAM™ Dressing | 56 | 5 | 66 | Hexagon | 1.1 | 10 | 7.5 |
| Grey Foam | N/A | 3 | N/A | Horizontal stripes | N/A | N/A | 7.2 |
| Zotefoam | 52 | 3 | 52 | Circular | 1 | 20 | 6.8 |
| V.A.C. ® GRANUFOAM™ Dressing | N/A | 3 | N/A | Horizontal Striping | N/A | N/A | 6.6 |
| V.A.C. ® GRANUFOAM™ Dressing | 52 | 5 | 52 | Circular | 1 | 20 | 6.5 |
| V.A.C. ® GRANUFOAM™ Dressing | N/A | 5 | N/A | Vertical Stripes | N/A | N/A | 6.1 |
| V.A.C. ® GRANUFOAM™ Dressing | N/A | 1 | N/A | None | N/A | N/A | 5.9 |
| V.A.C. ® GRANUFOAM™ Dressing | N/A | 3 | N/A | Vertical stripes | N/A | N/A | 5.6 |
| V.A.C. ® GRANUFOAM™ Dressing | 52 | 1 | 37 | None | 1 | 10 | 5.5 |

In some embodiments, the formulas described above may not precisely describe the lateral forces due to losses in force due to the transfer of the force from the contact layer to the wound. For example, the modulus and stretching of the cover 116, the modulus of the tissue site, slippage of the cover 116 over the tissue site, and friction between the contact layer 202 and the tissue site may cause the actual value of the lateral force 504 to be less than the calculated value of the lateral force 504.

Figure 11:
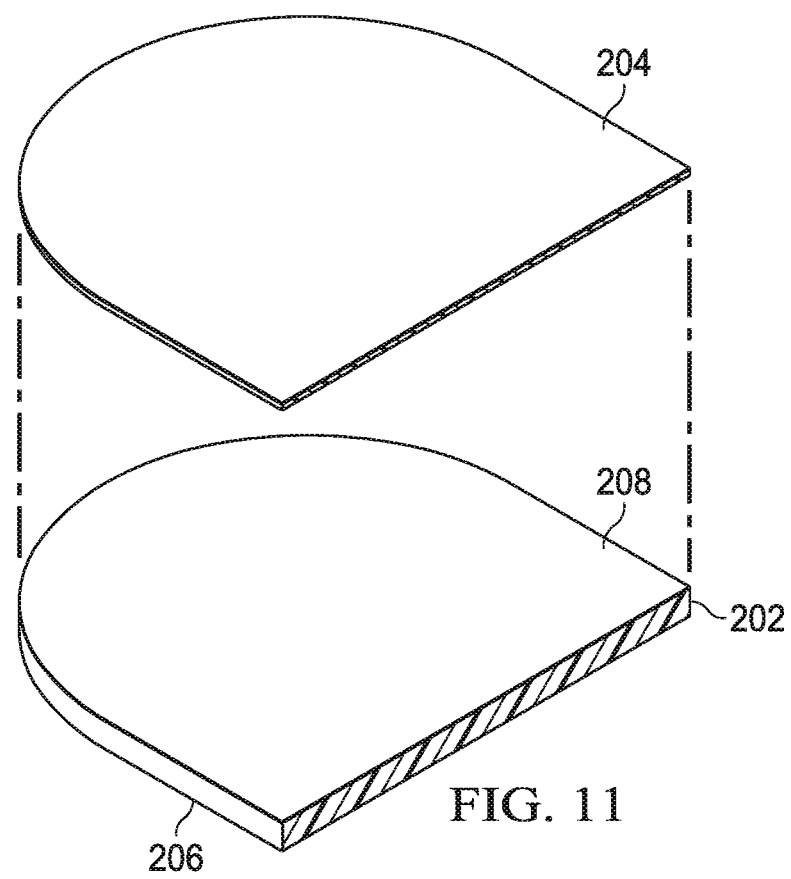
FIGS. 11-16 are schematic views of a process for manufacturing the tissue interface of FIG. 2, illustrating additional details that may be associated with some embodiments.
Figure 12:
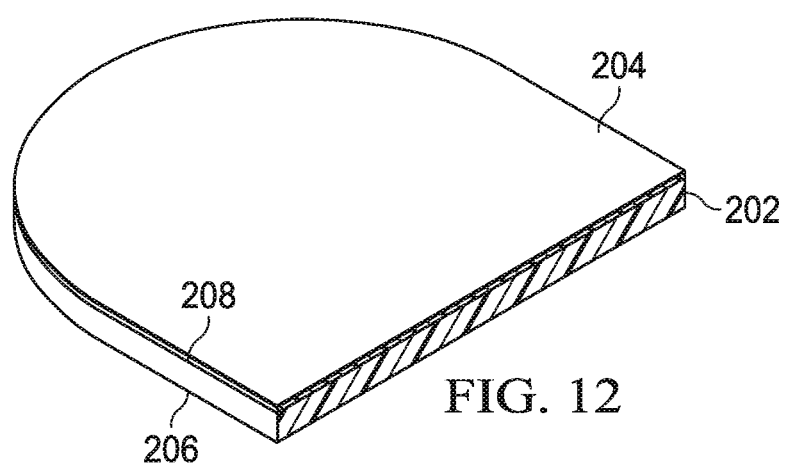

FIG. 11 is a perspective assembly view illustrating additional details that may be associated with a process for manufacturing the tissue interface 114. The contact layer 202 can be provided as a compressed foam layer free from the through-holes 210. The adhesive layer 204 can be brought proximate to the contact layer 202. In some embodiments, the contact layer 202 and the adhesive layer 204 can be coincident. While the contact layer 202 and the adhesive layer 204 are illustrated as having a rectangular shape with a circular end, the contact layer 202 and the adhesive layer 204 may have other shapes and sizes and may be cut after final assembly to a desired shape. FIG. 12 is a perspective view illustrating additional details that may be associated with the process for manufacturing the tissue interface 114. In some embodiments, the adhesive layer 204 can be coupled to the contact layer 202. For example, the adhesive layer 204 may have a tackiness that adheres the adhesive layer 204 to the contact layer 202. In other embodiments, the adhesive layer 204 may be bonded or otherwise secured to the contact layer 202.

Figure 13:
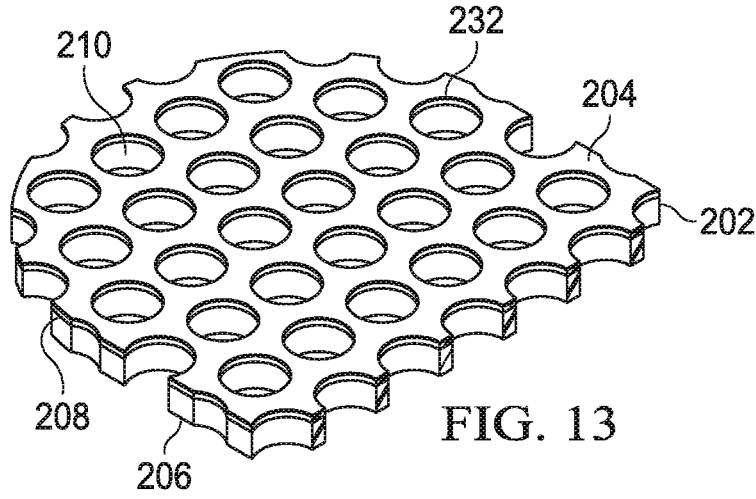
Figure 14:
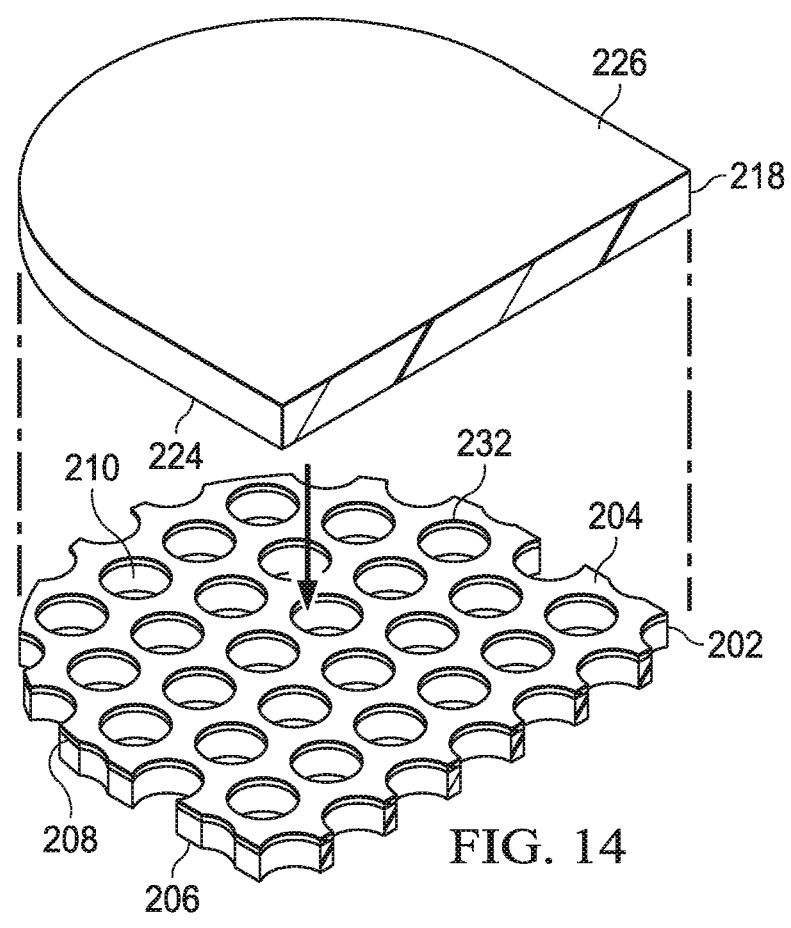

FIG. 13 is a perspective view illustrating additional details that may be associated with the process for manufacturing the tissue interface 114. After the adhesive layer 204 is bonded to the contact layer 202, the through-holes 210 and the through-holes 232 may be formed. For example, the contact layer 202 and the adhesive layer 204 can be die cut and the slugs removed. In other embodiments, the through-holes 210 and the through-holes 232 can be formed by vaporization, melting, laser-cutting, or other material removal mechanisms. FIG. 14 is a perspective view illustrating additional details that may be associated with the process for manufacturing the tissue interface 114. The first retainer layer 218 can be brought adjacent to the assembled contact layer 202 and the adhesive layer 204. The first retainer layer 218, the contact layer 202, and the adhesive layer 204 can be heated and compressed. For example, the contact layer 202, the adhesive layer 204, and the first retainer layer 218 can be placed into a heated platen press and compressed. Preferably, the compression and heat applied to the first retainer layer 218 and the contact layer 202 are less than the compression and heat necessary to induce felting in the material of the first retainer layer 218 and the contact layer 202. The combination of heat and compression can activate the adhesive layer 204, coupling the first retainer layer 218 to the contact layer 202.

Figures 15, 16:
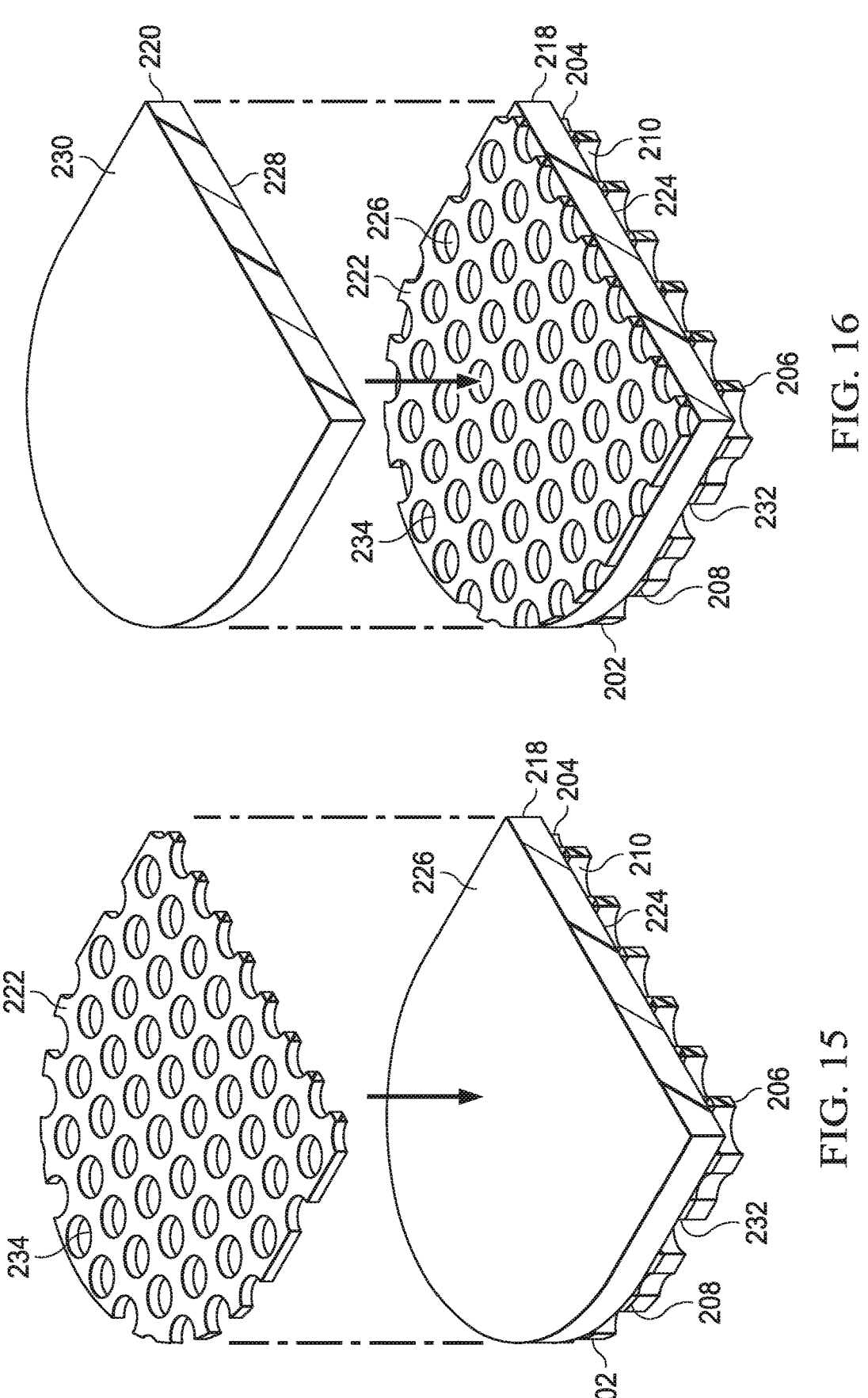

FIG. 15 is a perspective view illustrating additional details that may be associated with the process for manufacturing the tissue interface 114. The coupling layer 222 can be positioned proximate the second surface 226 of the first retainer layer 218. The first adhesive 304 of the coupling layer 222 can be brought adjacent to the second surface 226 of the first retainer layer 218, coupling the coupling layer 222 to the first retainer layer 218. FIG. 16 is a perspective view illustrating additional details that may be associated with the process for manufacturing the tissue interface 114. The second retainer layer 220 can be positioned proximate to the coupling layer 222. In some embodiments, the first surface 228 of the second retainer layer 220 can be positioned adjacent to the second adhesive 306 of the coupling layer 222. The coupling layer 222 can releasably couple the second retainer layer 220 to the first retainer layer 218.

Figure 17:
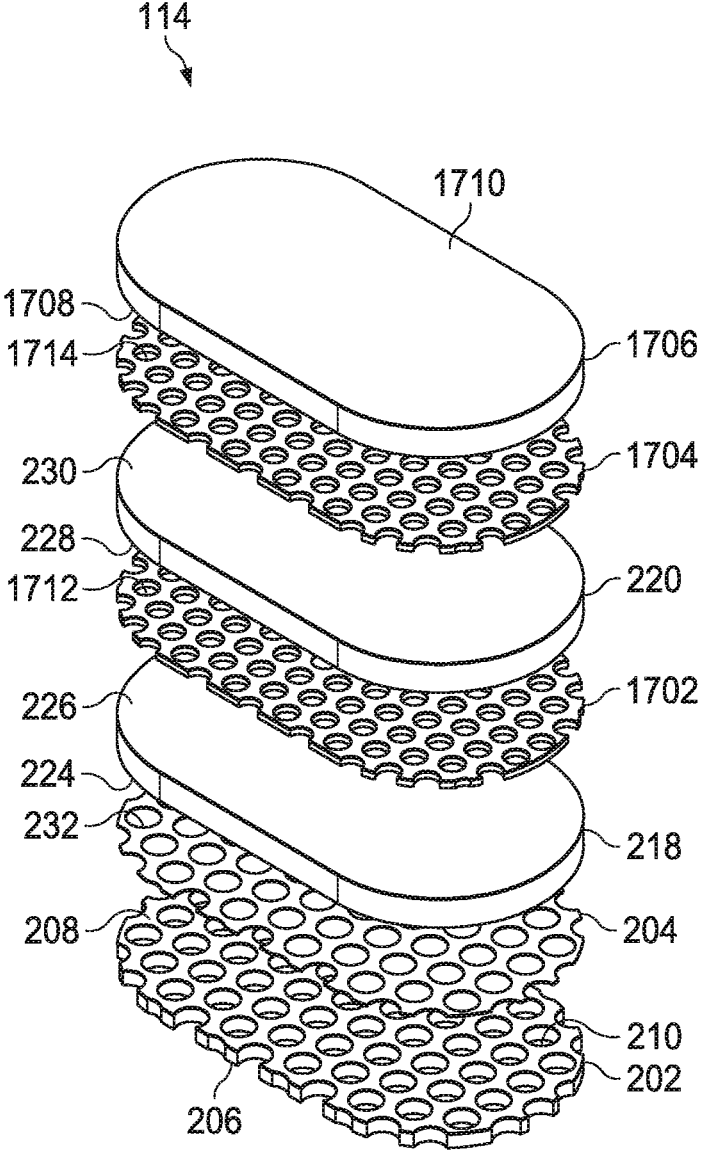
FIG. 17 is an assembly view of an example of the tissue interface of FIG. 1, illustrating additional details that may be associated with another embodiment in which the tissue interface comprises multiple layers.

FIG. 17 is an assembly view of an example of the tissue interface 114 of FIG. 1, illustrating additional details that may be associated with some embodiments in which the tissue interface 114 comprises multiple layers. In some embodiments, the tissue interface 114 can include the contact layer 202, the adhesive layer 204, the first retainer layer 218, a first coupling layer 1702, the second retainer layer 220, a second coupling layer 1704, and a third retainer layer 1706. The contact layer 202 may have the first surface 206, the second surface 208, and the plurality of through-holes 210 extending through the contact layer 202 from the first surface 206 to the second surface 208. The adhesive layer 204 may include the plurality of through-holes 232 and may be disposed adjacent to the second surface 208 of the contact layer 202. In some embodiments, the adhesive layer 204 can be coupled to the second surface 208 of the contact layer 202.

The first retainer layer 218 may have the first surface 224 and the second surface 226. The second retainer layer 220 may have the first surface 228 and the second surface 230. In some embodiments, the adhesive layer 204 can be coupled to the first surface 224 of the first retainer layer 218. The first coupling layer 1702 may couple the first retainer layer 218 to the second retainer layer 220. The second surface 226 of the first retainer layer 218 may be coupled to the first coupling layer 1702, and the first surface 228 of the second retainer layer 220 may be coupled to the first coupling layer 1702. The adhesive layer 204 may be disposed adjacent to the first surface 224 of the first retainer layer 218. The third retainer layer 1706 may have a first side 1708 and a second surface 1710. The second coupling layer 1704 may be coupled to the second surface 230 of the second retainer layer 220, and the first side 1708 of the third retainer layer 1706 may be coupled to the second coupling layer 1704.

In some embodiments, the third retainer layer 1706 may be a foam having pore sizes in a range of about 60 microns to about 2000 microns. In other embodiments, the third retainer layer 1706 may be a foam having pore sizes in a range of about 400 microns to about 600 microns. The tensile strength of the third retainer layer 1706 may also vary according to needs of a prescribed therapy. For example, the tensile strength of a foam may be increased for instillation of topical treatment solutions. The 25% compression load deflection of the third retainer layer 1706 may be at least 0.35 pounds per square inch, and the 65% compression load deflection may be at least 0.43 pounds per square inch. In some embodiments, the tensile strength of the third retainer layer 1706 may be at least 10 pounds per square inch. The third retainer layer 1706 may have a tear strength of at least 2.5 pounds per inch. In one non-limiting example, the third retainer layer 1706 may be an open-cell, reticulated polyurethane foam such as V.A.C.® GRANUFOAM® Dressing available from Kinetic Concepts, Inc. of San Antonio, Texas; in other embodiments the third retainer layer 1706 may be an open-cell, reticulated polyurethane foam such as a V.A.C. VERAFLO™ dressing, also available from Kinetic Concepts, Inc., of San Antonio, Texas. In other embodiments, the third retainer layer 1706 may be formed of an un-reticulated open-cell foam.

The first coupling layer 1702 and the second coupling layer 1704 may be similar to and include the elements of the coupling layer 222. The first coupling layer 1702 may have a plurality of perforations 1712, and the second coupling layer 1704 may have a plurality of perforations 1714. Each of the first coupling layer 1702 and the second coupling layer 1704 may comprise a film layer, a first adhesive 4, and a second adhesive. The film layer may be a polyurethane film having a thickness between about 25 microns and about 50 microns and preferably about 40 microns. The first adhesive may have a bond strength of less than about 0.5N/25 mm and a coating weight of about 150 g.s.m. The second adhesive may have a bond strength of about 8.0N/25 mm and a coating weight of about 40 g.s.m.

The perforations 1712 and the perforations 1714 may comprise separate perforations in each layer of the first coupling layer 1702 and the second coupling layer 1704. The perforations 1712 and the perforations 1714 may each have an average effective diameter of about 1.6 mm and a pitch of about 0.06 inches. In some embodiments, the first coupling layer 1702 and the second coupling layer 1704 may be a Vancive Medical MED6501SI Double-Coated, Trilaminate Polyurethane Film with Soft Silicone Adhesive.

Figure 18:
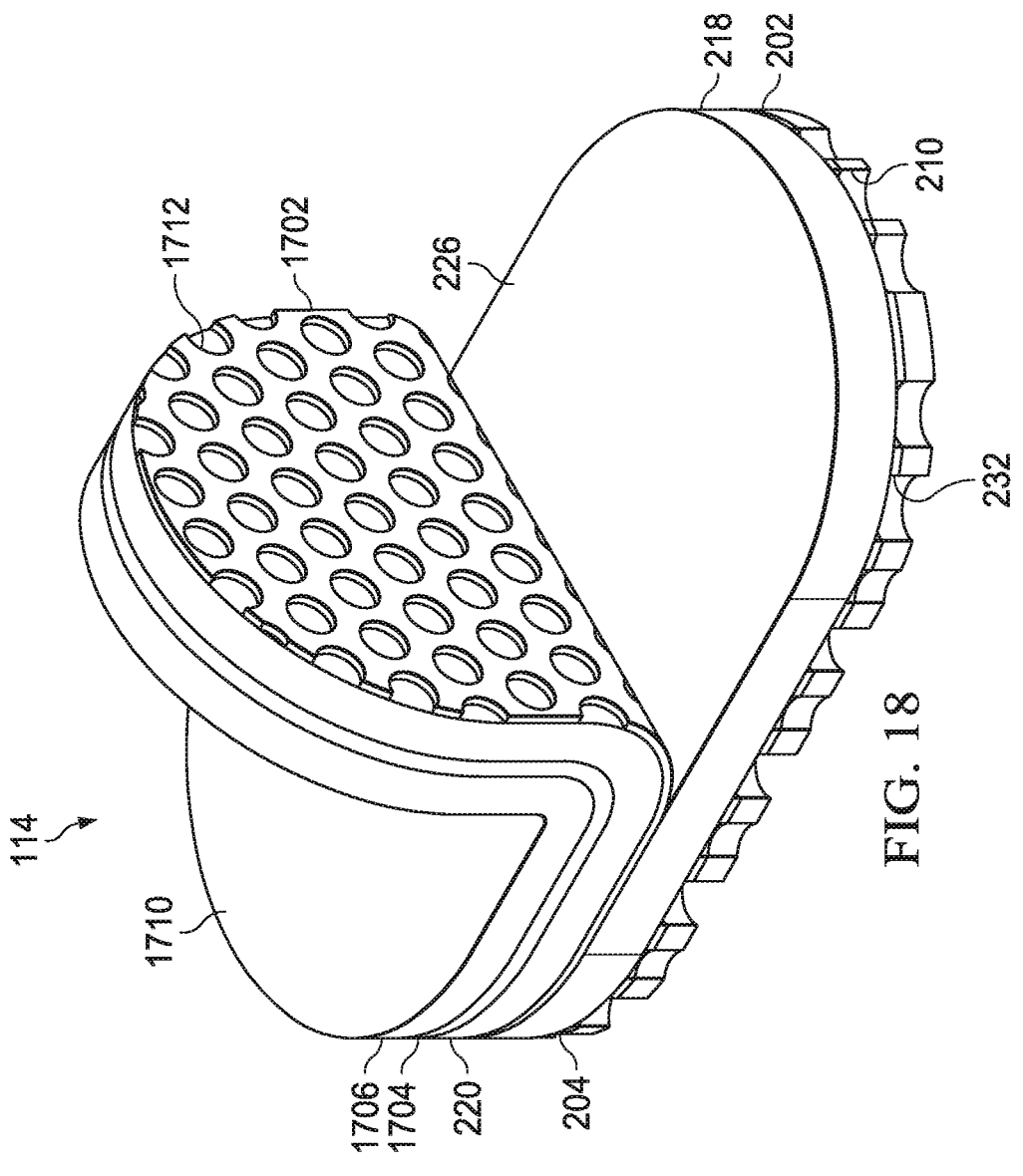
FIG. 18 is a perspective view of the tissue interface of FIG. 17, illustrating additional details that may be associated with removal of a portion of the tissue interface.

FIG. 18 is a perspective view of the tissue interface 114 of FIG. 17, illustrating additional details that may be associated with some embodiments. As illustrated in FIG. 18, the second retainer layer 220 and the third retainer layer 1706 may be removed from the tissue interface 114. For example, the second retainer layer 220 may be peeled from the tissue interface 114, removing the second retainer layer 220 and the third retainer layer 1706. Similarly, the third retainer layer 1706 could be peeled from the tissue interface 114, removing the third retainer layer 1706 from the tissue interface 114. The first coupling layer 1702 and the second coupling layer 1704 may be similar to and include the elements of the coupling layer 222 of FIG. 2. Each of the first coupling layer 1702 and the second coupling layer 1704 may have the first adhesive 304 and the second adhesive 306. The second adhesive 306, being stronger than the first adhesive 304, may maintain the coupling of the first coupling layer 1702 and the second coupling layer 1704 to the overlying layer, for example, the second retainer layer 220 and the third retainer layer 1706, respectively. If the overlying layer is removed, the first adhesive, having a lower bond strength, will break or fail before the second adhesive, retaining the respective coupling layer to the overlying retainer layer.

In some embodiments, a tissue interface, such as the tissue interface 114 of FIG. 2 and FIG. 17, may include a plurality of sizing perforations, permitting the tissue interface 114 to be sized without the use of additional tools. For example, the tissue interface 114 may include a plurality of sizing perforations extending through the tissue interface 114 from the second surface 1710 of the third retainer layer 1706 to the first surface 206 of the contact layer 202. In other embodiments, the sizing perforations may extend through a portion of the tissue interface 114. For example, the sizing perforations may extend through the third retainer layer 1706, the second retainer layer 220, the first retainer layer 218, and a portion of the contact layer 202. In another example, the sizing perforations may extend through the contact layer 202 and a portion of one or more of the third retainer layer 1706, the second retainer layer 220, and the first retainer layer 218. The sizing perforations may permit a user to tear the tissue interface 114 along the sizing perforations to decrease a length and width of the tissue interface. For example, the sizing perforations may separate portions of the tissue interface 114 from adjacent portions of the tissue interface 114, leaving one or more tabs connecting the portions of the tissue interface 114. The tabs may have a size that may be an order of magnitude less than a corresponding size of the sizing perforations. In some embodiments, the sizing perforations may be a spiral cut in the tissue interface 114 originating near a center of the tissue interface 114 and emanating outward.

In some embodiments, the sizing perforations be may be cubed sizing perforations. For example, the tissue interface 114 may have a plurality of sizing perforations formed in the tissue interface 114 from the second surface 1710 of the third retainer layer 1706 to the first surface 206 of the contact layer 202. The plurality of sizing perforations may be arranged so that the sizing perforations create cubes within the tissue interface 114 that may be removable from the remainder of the tissue interface 114. In some embodiments, the cubes may be removed by tearing, cutting, or otherwise separating the cubes from the remainder of the tissue interface 114. For example, cubes may be removed from edges of the tissue interface 114 to decrease a length and width of the tissue interface 114 to permit the tissue interface 144 to be placed within a tissue site that is smaller than the tissue interface 114 prior to removal of the cubes. In other embodiments, the cubed sizing perforations may permit removal of a portion of the tissue interface 114 in overlaying areas of a tissue site having variable topography. The removed portions of the tissue interface 114 may be aligned with raised topographical portions of the tissue site, permitting the tissue interface 114 to lay flat within the tissue site.

The systems, apparatuses, and methods described herein may provide significant advantages. For example, the embodiments described herein provide a multi-layered tissue interface that is easier to apply to a tissue site, can provide improved healing/wound cleansing, and reduce improper placement of the tissue interface. The tissue interface described herein can also be used on sensitive tissue areas. For example, during sizing of the dressing, the user may place the entirety of the dressing at the tissue site, remove one or more layers, or cut each layer of the dressing simultaneously rather than individually.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, the dressing comprising:
   a contact layer formed from a porous material and having a first side and a second side, the first side configured to be positioned adjacent to the tissue site, the contact layer having a plurality of holes extending through the contact layer from the first side to the second side;

a cover layer formed from a porous material and having a first side and a second side, the first side coupled to the contact layer; and at least one retainer layer formed from a porous material, the at least one retainer layer removably coupled to the second side of the cover layer.

2. The dressing of claim 1, wherein the cover layer is adhered to the contact layer.

3. The dressing of claim 1, wherein the cover layer is coupled to the contact layer using a hot-melt adhesive.

4. The dressing of claim 1, wherein the at least one retainer layer is hydrophilic.

5. The dressing of claim 1, wherein the at least one retainer layer is hydrophobic.

6. The dressing of claim 1, wherein the at least one retainer layer comprises a first retainer layer and a second retainer layer, wherein the first retainer layer is removably coupled to the cover layer and the second retainer layer is removably coupled to the first retainer layer.

7. The dressing of claim 1, wherein the at least one retainer layer has a first side and a second side, the dressing further comprising a polyurethane film layer, the polyurethane film layer having a plurality of perforations, a first adhesive on a first side, and a second adhesive on a second side, the second adhesive of the polyurethane film layer adjacent to the first side of the at least one retainer layer.

8. The dressing of claim 7, wherein the second adhesive has a higher bond strength than the first adhesive.

9. The dressing of claim 7, wherein the at least one retainer layer is configured to be removed from the cover layer and the second adhesive is configured to retain the polyurethane film layer and the first adhesive with the at least one retainer layer.

10. The dressing of claim 1, wherein the cover layer is permanently coupled to the contact layer.

11. The dressing of claim 1, further comprising an adhesive layer disposed between the contact layer and the cover layer, the adhesive layer adhering the contact layer to the cover layer.

12. The dressing of claim 11, wherein the adhesive layer comprises a hot-melt adhesive.

13. The dressing of claim 1, wherein:

the contact layer is formed from a felted open-cell reticulated foam;

the cover layer is formed from an open-cell reticulated foam; and the at least one retainer layer is formed from an open-cell reticulated foam.

* * * * *